US008586799B2

(12) United States Patent
Nandy et al.

(10) Patent No.: US 8,586,799 B2
(45) Date of Patent: Nov. 19, 2013

(54) COMPOUNDS AND METHODS FOR PREPARATION OF DIARYLPROPANES

(75) Inventors: Sandip K. Nandy, Olympia, WA (US); Abeysinghe Arrachchigae Padmapriya, Olympia, WA (US)

(73) Assignee: Unigen, Inc., Seattle, WA (US)

( * ) Notice: Subject to any disclaimer, the term of this patent is extended or adjusted under 35 U.S.C. 154(b) by 47 days.

(21) Appl. No.: 13/425,959

(22) Filed: Mar. 21, 2012

(65) Prior Publication Data

US 2012/0245393 A1   Sep. 27, 2012

Related U.S. Application Data

(60) Provisional application No. 61/467,286, filed on Mar. 24, 2011.

(51) Int. Cl.
*C07C 49/84* (2006.01)
*C07C 45/00* (2006.01)

(52) U.S. Cl.
USPC .......................................... 568/331; 568/334

(58) Field of Classification Search
USPC ................................................ 568/331, 334
See application file for complete search history.

(56) References Cited

U.S. PATENT DOCUMENTS

| | | | |
|---|---|---|---|
| 1,596,613 A | 8/1926 | Klarmann |
| 3,133,967 A | 5/1964 | Ernst et al. |
| 4,678,664 A | 7/1987 | Schmolka |
| 5,071,835 A | 12/1991 | Guidon |
| 5,430,062 A | 7/1995 | Cushman et al. |
| 5,545,399 A | 8/1996 | Lee et al. |
| 5,719,306 A | 2/1998 | Chandrakumar et al. |
| 5,880,314 A | 3/1999 | Shinomiya et al. |
| 6,093,836 A | 7/2000 | Rhee et al. |
| 6,214,874 B1 | 4/2001 | Huang et al. |
| 6,221,604 B1 | 4/2001 | Upadhya et al. |
| 6,296,857 B1 | 10/2001 | Schonrock et al. |
| 6,355,683 B1 | 3/2002 | Baell et al. |
| 6,562,791 B1 | 5/2003 | Maurya et al. |
| 7,767,661 B2 | 8/2010 | Jia et al. |
| 8,362,305 B2 | 1/2013 | Nandy et al. |
| 2002/0044914 A1 | 4/2002 | Dooley et al. |
| 2002/0052410 A1 | 5/2002 | Steiner et al. |
| 2003/0027810 A1 | 2/2003 | Efange |
| 2004/0016063 A1 | 1/2004 | Chassot et al. |
| 2005/0267047 A1 | 12/2005 | Jia et al. |
| 2006/0178356 A1 | 8/2006 | Wang et al. |
| 2007/0098655 A1 | 5/2007 | Schmaus et al. |
| 2008/0032938 A1 | 2/2008 | Saliou et al. |
| 2008/0132581 A1 | 6/2008 | Jia et al. |
| 2010/0016347 A1 | 1/2010 | Nandy et al. |
| 2010/0267839 A1 | 10/2010 | Jia et al. |

FOREIGN PATENT DOCUMENTS

| | | |
|---|---|---|
| CA | 238730 A | 3/1924 |
| CN | 139217 A | 1/2003 |
| CN | 1439643 A | 9/2003 |
| CN | 1462739 A | 12/2003 |
| EP | 0 297 733 | 1/1989 |
| EP | 1191030 A2 | 3/2002 |
| EP | 1015446 | 4/2003 |
| JP | 4906311 B | 2/1974 |
| JP | 5758610 A | 4/1982 |
| JP | 05-213729 A | 8/1993 |
| JP | 08337510 | 12/1996 |
| JP | 2000/095721 | 4/2000 |
| JP | 2002/047132 A | 2/2002 |
| JP | 2002/193990 A | 7/2002 |
| RU | 2156771 C2 | 9/2000 |
| WO | 88/03026 | 5/1988 |
| WO | 88/03800 | 6/1988 |
| WO | 93/23357 | 11/1993 |
| WO | 94/05682 | 3/1994 |
| WO | 98/39279 | 9/1998 |
| WO | 01/30148 | 5/2001 |
| WO | 02/02096 | 1/2002 |
| WO | 02/32379 | 4/2002 |
| WO | 02/34718 | 5/2002 |
| WO | 02/35580 | 5/2002 |
| WO | 03/009807 | 2/2003 |
| WO | 03/040077 | 5/2003 |
| WO | 03/049713 | 6/2003 |
| WO | 03/086414 | 10/2003 |

OTHER PUBLICATIONS

Klarmann, Emil, "Preparation of 2,4-didydroxydiphenylmethane and of 2,4-dihydroxydiphenylethane," *Journal of the American Chemical Society* 48:791-794, 1926. Database CAPLUS on STN, Acc. No. 1926:9814.

Reimann, Eberhard, "Natural stilbenes. Synthesis of polyhydroxystilbene ethers by the Wittig reaction," *Chemische Berichte* 102(9):2881-2888, 1969. Database CAPLUS on STN, Acc. No. 1969:501457.

(Continued)

*Primary Examiner* — Sikarl Witherspoon
(74) *Attorney, Agent, or Firm* — Seed IP Law Group PLLC

(57) ABSTRACT

Compounds of structure (I):

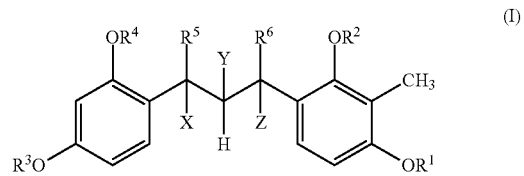

including stereoisomers, tautomers and salts thereof, wherein $R^1$, $R^2$, $R^3$, $R^4$, $R^5$, $R^6$, X, Y and Z are as defined herein. Such compounds are useful for the preparation of diarylpropane compounds. Methods for the preparation of compounds of structure (I) are also disclosed, as are methods employing compounds of structure (I) for the preparation of diarylpropanes.

59 Claims, No Drawings

(56) References Cited

OTHER PUBLICATIONS

Da Silva et al., "1,3-Diarylpropanes from *Iryanthera paraensis* and *Iryanthera tricornis*," *Acta Amazonica* 14(3-4):455-457, 1984. Database CAPLUS on STN, Acc. No. 1987:15698.

Tandon et al., "A bibenzyl xyloside from *Chlorophytum arundinaceum*," *Phytochemistry* 32(6):1624-1625, 1993. Database CAPLUS on STN, Acc. No. 1993:513368.

Dol et al., "Binding properties of two novel phosphine-modified tetrapodants and their bimetallic transition metal complexes," *European Journal of Inorganic Chemistry* 12:1975-1985, 1998. Database CAPLUS on STN, Acc. No. 1998:771697.

Ando et al., "Cyclization Reactions of 2,3-Bis (2-Cyanophenyl) Propionitriles. III. Substituent Effect on the Carbanion Reactives of the Propionitriles and Tautomerism of 5-Acetomido-11-Cyanoindeno[L,2-C]Isoquinolines," *Bulletin of the Chemical Society of Japan, Chemical Society of Japan*, 53(10):2885-2890, 1980.

Anjaneyulu et al., "Nordihydroguairetic Acid, A Lignin, Prevents Oxidative Stress and the Development of Diabetic Nephropathy in Rats," *Pharmacology* 72(I): 42-50, 2004.

Anonymous, "CGP-61755 (Lasinavir (234416))," *Annual Drug Data Report* 18(6):553, 1996.

Bezuidenhout et al., "hydroxydihydrochalcones and Related 1,3-Diarylpropan-2-ones from *Xanthocercis zambesiaca*," *Phytochem.* 27(7):2329-2334, 1988.

Bohlmann, et al., "Neue Chalkon-Derivate Aus Sudafrikanischen Helichrysum-Arten," *Phytochem* 17:1935-1937, 1978.

Braz F. et al., "Diarylpropanoid from *Virola multinervia*," *Phytochem.* 15:567-568, 1976.

Braz Filho et al., "Flavonoids from *Iryanthera laevis*," *Phytochem.* 19:1195-1197, 1980.

Calas et al., "Synthese d'analogues noveaux de la trimethoprime Etude de relation structure-activite antibacterienne," *Eur. J. of Med. Chem..* 17(6):497-504, 1982.

Carpenter et al., "Synthesis of Molecular Units for Rational Synthesis of Phenol-Formaldehyde and Allied Resins. I. Synthesis of Resoles, Dihydroxydiphenylethanes, and Dihydroxydiphenylpropanes," *J. Appl. Chem.* 1:217-226, 1951.

De Almeida et al., "Diarylpropanoids from *Iryanthera polynerua*," *Phytochem.* 18:1015-1016, 1979.

Diaz D. et al., "Diarylpropanes from the Wood of *Iryanthera grandis*," *Phytochem.* 25(10):2395-2397, 1986.

Gonzalez et al., "Stilbenes and other Constituents of *Knema austrosiamensis*," *Phytochem.* 32(2):433-438, 1993.

Goodson et al., "Analgesics. III. Hydrochlorides of Phenylalkylamines," *Journal of the American Chemical Society* 71(9):3219-3221, 1949.

Hagos et al., "Isolation of Smooth Muscle Relaxing 1,3-Diarylpropan-2-ol Derivatives from *Acacia tortilis*," *Planta Med.* 53:27-31, 1987.

Iida et al., "Sensitive Screening of Antfungal Compounds from Acetone Extracts of Medicinal Plants with a Bio-Cell Tracer," *Yakugaku Zasshi* 119:964-971, 1999.

Ikuta et al., "Components of *Broussonetia kazinoki* SIEB. I. Structure of Two New Isoprenylatd Flavans and Five New Isoprenylated 1,3-Diphenylpropane Derivatives," *Chem. Pharm. Bull.* 34:1968-1979, 1986.

Jang et al., "Melanogenesis Inhibitor from paper Mulberry," *Cosmetics & Toiletries* 112:59-62, 1997.

Jia et al., "Diarylpropanes as a novel class of potent tyrosinase inhibitors and their biological properties," *Journal of Investigative Dermatology* 127(suppl. 1):S151, 2007.

Kato et al., "Components of *Broussonetia kazinoki* SIEB. (2). Structures of Four New Isoprenylated 1,3-Diphenylpropane Derivatives," *Chem Pharm. Bull* 34:2448-2455, 1986.

Kijjoa et al., "1,3-Diaryl-Propanes and Propan-2-ols from *Virola* Species," *Phytochem.* 20(6):1385-1388, 1981.

Ko et al., "Cytotoxic Isoprenylated Flavans of *Broussonetia kazinoki*," *J. Nat. Prod.* 62:164-166, 1999.

Kuck et al., "Hydrogen Rearrangement in Molecular Ions of Alkyl Benzenes: Mechanism and Time Dependence of Hydrogen Migrations in Molecular Ions of 1,3-Diphenylpropane and Deuterated Analogues," *Organic Mass Spectrometry* 13(2):90-102, 1978.

Lee et al., "Aromatase Inhibitors from *Broussonetia paprifera*," *J. Nat. Prod.* 64:1286-1293, 2001.

Lee et al., "Hydrogen-Deuterium Exchanges in a Friedel-Crafts Reaction," *Journal of Organic Chemistry* 50:705-707, 1985.

Leong et al., "1-(2-Hydroxy-3,4,5,6-Tetramethoxyphenyl)-3-Phenylpropene From *Lindera lucida*," *Phytochemistry* 49(7):2141-2143, 1998.

Lin et al., "Phenolic Glycosides from *Viscum anagulatum*," *J. Nat. Prod.* 65:638-040, 2002.

Matubara et al., "Inhibitory effect of Lichen Metabolites and Their Synthetic Analogs on Melanin Biosynthesis in Cultured B-16 Mouse Melanoma Cells," *Natural Product Sciences* 4(3):161-169, 1998.

Maurya et al., "The Synthesis of Propetrol, a Novel 1,3-Diarylpropan-2-ol from *Pterocarpus marsupium*," *J. Nat. Prod.* 48(2):313-315, 1985.

Morimoto et al., "Tannins and related Compounds. XXIX.1Seven New Methyl Derivatives of Flavan-3-ols and 1,3-Diarylpropane-2-ol from *Cinnamomum cassia, C. obtusifolium* and *Lindera umbellate* var. *membranacea*," *Chem. Pharm. Bull.* 33:2281-2286, 1985.

Morais, et al., "Synthesis of Three Natural 1,3-Diarylpropanes: Two Revised Structures," *Phytochemistry* 28(1):239-242, 1989.

Moss et al., "Peptidomimetic Inhibitors of herpes Simplex Virus Ribonucleotide Reductase: A New Class of Antiviral Agents," *Journal of Medicinal Chemistry* 38(18):3617-3623, 1995.

Nandy et al., "A convenient method for the syntheses of tetrahydrofuran moiety from furan by catalytic transfer of hydrogenation with ammonium formate," *Tetrahedron Letters* 49:2469-2471, 2008.

Napolitano et al., "Inhibitory effect of melanin precursors on arachidonic acid peroxidation," *Biochimica et Biophysica Acta* 1168:175-180, 1993.

Ohguchi et al., "Effects of Hydroxystilbene Derivatives on Tyrosinase Activity," *Biochemical and Biophysical Research Communications* 307(4):861-863, 2003.

Ohguchi et al., "Inhibitory Effects of Resveratrol Derivatives from Dipterocarpaceae Plants on Tyrosinase Activity," *Bioscience, Biotechnology and Biochemistry* 67(7):1587-1589, 2003.

Pettit et al., Antineoplastic Agents 440. Asymmetric Synthesis and Evaluation of the Combretastatin A-I SAR Probes (1S,2S)-And (1R,2R)-1,2-Dihydroxy-1-(2',3'-dihydroxy-4'-methoxyphenyl)-2(3",4",5"-trimethoxyphennyl)-ethane, *Journal of Natural Products* 63(7):969-974, 2000.

Rao et al., "Propterol: A 1,3-Diarylpropan-2—ol from *Pterocarpus marsupium*," *Phytochemistry* 23(4):897-898, 1984.

Shimizu et al., "Inhibition of Tyrosinase by Flavonoids, Stilbenes and Related 4-Substituted Resorcinols: Structure-Activity Investigations," *Planta Medica* 66(I):11-15, 2000.

Silva et al., "Dihydrochalcones and Flavonolignans from *Iryanthera lancifolia*," *J. Nat. Prod.* 62(11)1475-1478, 1999.

Stedman's Medical Dictionary: "Melanin," Twenty-Second Edition, p. 755, col. 2, lines 16-25, 1972.

Stuart et al., "2,4-Diamino-5-Benzylpyrimidineasn and Analogues as Antibacterial Agents. 6. A One-Step Synthesis of New Trimethoprim Derivatives and Activity Analysis by Molecular Modeling," *Journal of Medicinal Chemistry* 26(5):667-673, 1983.

Takasugi et al., "Eight Minor Phytoalexins from Diseased paper Mulberry," *Chem Lett.* 689-692, 1984.

Talukdar et al., "An isoflavone from *Myristica malabarica*," *Phytochemistry* 53:155-157, 2000.

Tsuchiya et al., "Anti-Candida Activity of Synthetic Hydroxychalcones," *Die Pharmazie* 49(10):756-758, 1994.

Williams and Lemke, Foyes' Principles of Medicinal Chemistry, Fifth Ed., 60-61, 2002.

Wu et al., "Total Synthesis of Nordihydroguaiaretic Acid," *Acat Pharmaceutica Sinica* 32(4):278-281, 1997. (abstract).

Yoshitomi et al., "Cosmetics Containing Hydrochalcone Glycosides," & JP 2002 193990A (Japan) (Abstract), 2002.

(56) References Cited

OTHER PUBLICATIONS

Zeng et al., "Kneglomeratonol, Kneglomeratanones A and B, and Related bioactive Compounds from *Knema glomerata*," *J. Nat. Prod.* 57(3):376-381, 1994.
Office Action issued Apr. 3, 2009 in U.S. Appl. No. 12/027,090.
Office Action issued Jan. 13, 1010, in U.S. Appl. No. 12/027,090.
International Search Report issued Nov. 10, 2005, in International Application Serial No. PCT/US2005/018884.
Written Opinion issued Nov. 10, 2005, in International Application Serial No. PCT/US2005/018884.
EP Search Report issued Nov. 21, 2008 in EP 05762186.4.
International Search Report and Written Opinion issued Sep. 16, 2009, in International Application Serial No. PCT/US2009/051217, 2 pages.
International Preliminary Report on Patentability and Written Opinion issued Jan. 25, 2011, in International Application Serial No. PCT/US2009/051217, 9 pages.
Office Action for Canadian Application No. 2,567,801.
Notification of First Office Action for corresponding Chinese Patent Application No. 201110080259.8, mailed Mar. 12, 2012.
English translation of Notification of First Office action for corresponding Chinese Patent Application No. 201110080259.8, mailed Mar. 12, 2012.
English Translation of Notification of First Office Action for corresponding Chinese Patent Application No. 200980128510.4, mailed Mar. 22, 2012, 5 pages.
Notification of First office Action for corresponding Chinese Patent Application No. 200980128510.4, mailed Mar. 22, 2012, 4 pages.
International Search Report and Written Opinion issued Aug. 14, 2012, in International Application Serial No. PCT/US2012/029875, 11 pages.
English translation of Japanese Reasons for Rejection for corresponding Japanese Patent Application No. 2007-515432.
U.S. Appl. No. 13/722,394, filed Dec. 20, 2012.
U.S. Appl. No. 13/707,270, filed Dec. 6, 2012.

COMPOUNDS AND METHODS FOR PREPARATION OF DIARYLPROPANES

CROSS-REFERENCE TO RELATED APPLICATION

This application claims the benefit under 35 U.S.C. §119(e) of U.S. Provisional Patent Application No. 61/467,286 filed Mar. 24, 2011, where this provisional application is incorporated herein by reference in its entirety.

BACKGROUND

1. Technical Field

The present invention is generally directed to compounds useful for the preparation of diarylpropanes and methods related to the same.

2. Description of the Related Art

There is great demand for products able to inhibit or prevent excessive pigmentation of the skin. Melanin, the skin's natural pigment, is a nitrogenous polymer synthesized in melanosomes, which are membrane-bound organelle present within melanocytes. Melanin is produced in varying concentrations, depending on skin type (genetic disposition) and environmental conditions. Melanocytes are cells that occur in the basal membrane of the epidermis, and account for between 5% and 10% of the cellular content (approximately 1200-1500 melanocytes/cm$^2$). When stimulated, by factors such as ultraviolet (UV) light, melanocytes divide more rapidly and produce greater quantities of melanin. The melanin is then transported in mature melanosomes to keratinocytes within the epidermis where it becomes visible as a brown skin color.

The over production of melanin can cause different types of abnormal skin color, hair color and other diseases and conditions of the skin. There are primarily two conditions related to skin pigmentation disorders. A darkening of the skin that includes abnormal elevated melanin caused by UV exposure and aging; and abnormal distribution of skin pigments resulting in age spots, liver spots, and drug and wound/disease induced hyperpigmentation (Seiberg et al. (2000) J. Invest. Dermatol. 115:162; Paine et al. (2001) J. Invest. Dermatol. 116:587).

Diarylalkanes are a rare class of natural product which have shown potential for decreasing melanin production and are being investigated for use as skin lightening therapeutics (see e.g., U.S. Pub. No. 2005/0267047). Although more than 179,000 natural compounds are listed in the Dictionary of Natural Products (Chapman & Hall/CRC, Version 12:2 Jan. 2004, available on CD-ROM), only 82 are diarylpropanes. Diarylpropanes have been isolated from a number of different natural sources; however, the low abundance of diarylpropanes of interest in natural sources often necessitates their preparation in the laboratory.

One approach for preparing diarylpropanes has been to completely reduce the corresponding chalcone to the diarylpropane in one step (see e.g., U.S. Pat. No. 5,880,314; J. Chem. Soc. Perkin Trans. 1 (1979), (7), 1661-4; and *Lett. In Org. Chem.* 2006, 3, 39-41. However, such methods are not robust and are unsuitable for large-scale preparation of diarylpropanes. For example, published methods generally suffer from low yields, poor reproducibility and result in mixtures of compounds which are difficult to separate. Methods and/or compounds to successfully address these, and other, difficulties associated with preparation of diarylpropanes have yet to be suggested.

While significant advances have been made in this field, there remains a need for improved methods for preparation of diarylpropanes as well as compounds useful for the same. In particular, methods and compounds suitable for large-scale preparation of diarylpropanes in high purity are needed. The present invention fulfills these needs, and provides other related advantages.

BRIEF SUMMARY

In brief, this invention is generally directed to compounds having the following structure (I):

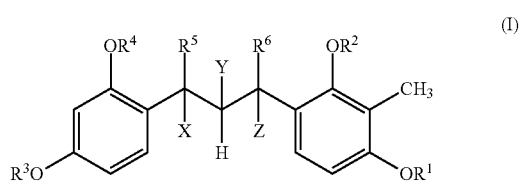

or a stereoisomer, tautomer or salt thereof, wherein $R^1$, $R^2$, $R^3$, $R^4$, $R^5$, $R^6$, X, Y and Z are as defined below.

Compounds of structure (I) above have utility over a wide range of applications. For example, the disclosed compounds may be used in methods for the preparation of diarylpropane compounds. Such methods result in better purity and higher yield of diarylpropane than other known methods. Accordingly, in one embodiment the present disclosure is directed to a method for preparation of diarylpropanes having the following structure (II):

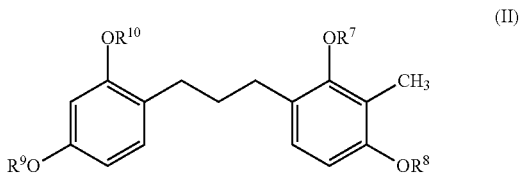

or a stereoisomer, tautomer or salt thereof, wherein $R^7$, $R^8$, $R^9$ and $R^{10}$ are as defined below. The method for preparation of compounds of structure (II) comprises reduction of compounds of structure (I). The robust character of the disclosed methods makes the methods more amenable to large-scale production of diarylpropanes compared to previous methods.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

As mentioned above, this invention is generally directed to compounds useful for the preparation of diarylpropanes, as well as to methods related to the same. In one embodiment, compounds are disclosed which have the following structure (I):

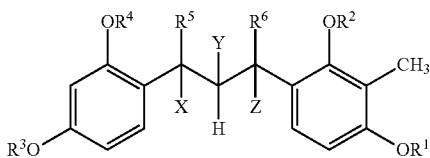

or a stereoisomer, tautomer or salt thereof, wherein:

$R^1$, $R^2$, $R^3$ and $R^4$ are each independently hydrogen, alkyl, aryl or aralkyl;

one of $R^5$ or $R^6$ is oxo, and the other of $R^5$ or $R^6$ is hydrogen; and

X, Y and Z are each independently absent or hydrogen, or X and Y or Z and Y may join to form a bond, wherein X, Y and Z are each chosen such that all valences are satisfied.

As used herein, the following terms have the meanings set forth below.

"Alkyl" means an optionally substituted, straight chain or branched, noncyclic or cyclic, unsaturated or saturated aliphatic hydrocarbon containing from 1 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Allyl" means an alkyl group, as defined above, comprising a methylene connected to a terminal alkene, for example —$CH_2CH=CH_2$.

"Alkoxy" means an alkyl moiety as defined above (i.e., an optionally substituted, straight chain or branched, noncyclic or cyclic, unsaturated or saturated aliphatic hydrocarbon containing from 1 to 10 carbon atoms) attached through an oxygen bridge (i.e., —O-alkyl) such as methoxy, ethoxy, and the like.

"Aryl" means an optionally substituted aromatic carbocyclic moiety such as phenyl, naphthyl and the like.

"Aralkyl" means one or more aryl moieties as defined above attached through an alkyl bridge (i.e., -alkyl-(aryl)$_n$, wherein n is 1, 2 or 3). Non-limiting examples of aralkyl moieties include benzyl (—$CH_2$-phenyl, i.e., Bn), diphenyl methyl (—$CH_2$—(phenyl)$_2$) and trityl (—C-(phenyl)$_3$).

"Heterocycle" (also referred to herein as a "heterocycle ring") means an optionally substituted 5- to 7-membered monocyclic, or an optionally substituted 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include "heteroaryl" which is an optionally substituted aromatic heterocycle ring of 5- to 10-members and having at least one heteroatom selected from nitrogen, oxygen and sulfur, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. Thus, in addition to the aromatic heteroaryls listed above, heterocycles also include (but are not limited to) morpholinyl, pyrrolidinonyl, pyrrolidinyl, piperizinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

An "optionally substituted" alkyl, aryl or aralkyl means an alkyl, aryl, or aralkyl moiety as defined above, wherein 0 to 4 hydrogen atoms of the aliphatic hydrocarbon or heterocycle are replaced with a substituent. When zero hydrogen atoms are replaced with a substituent, the alkyl, aryl, or aralkyl moiety is unsubstituted. When 1 to 4 hydrogen atoms are replaced with a substituent, the alkyl, aryl, or aralkyl moiety is substituted. In the case of an oxo substituent ("=O") two hydrogen atoms from the same carbon atom are replaced. When substituted, "substituents" within the context of this invention include oxo, halogen, hydroxyl, alkoxy or —$NR^aR^b$, wherein $R^a$ and $R^b$ are the same or different and independently hydrogen or alkyl moiety as defined above, or $R^a$ and $R^b$ are taken together with the nitrogen to which they are attached to form a heterocycle as defined above.

"Oxo" means =O (i.e., carbonyl).

"Hydroxyl" means —OH.

"Halogen" means fluoro, chloro, bromo and iodo.

In more specific embodiments of the compound of structure (I), $R^5$ is oxo, $R^6$ is hydrogen and the compound of structure (I) has one of the following structures (IA) or (IB):

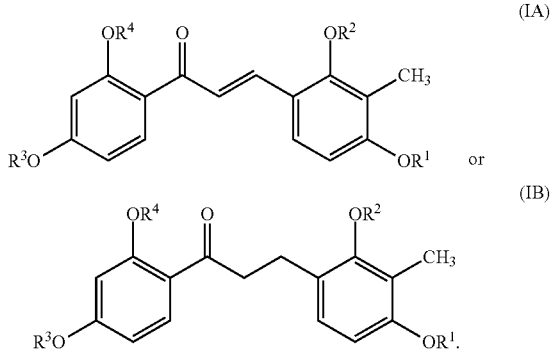

In other embodiments, each of $R^1$ and $R^2$ are alkyl. For example, in some aspects each of $R^1$ and $R^2$ are methyl and the compound of structure (I) has one of the following structures (IA-1) or (IB-1):

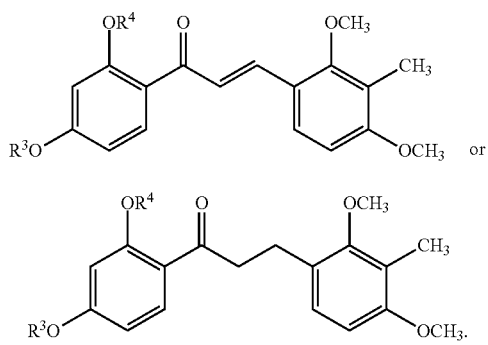

(IA-1)

(IB-1)

In some other embodiments, each of $R^3$ and $R^4$ are aralkyl. For example, in some embodiments, each of $R^3$ and $R^4$ are benzyl and the compound of structure (I) has one of the following structures (IA-2) or (IB-2):

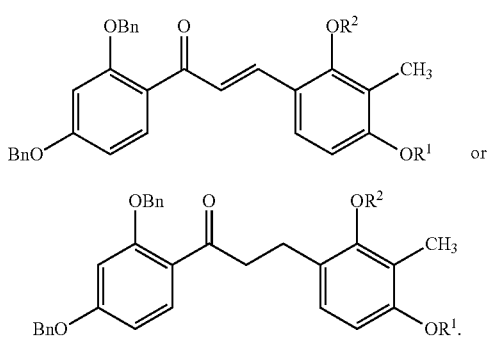

(IA-2)

(IB-2)

In yet other embodiments, each of $R^3$ and $R^4$ are alkyl. For example, in some aspects each of $R^3$ and $R^4$ are isopropyl and the compound of structure (I) has one of the following structures (IA-3) or (IB-3):

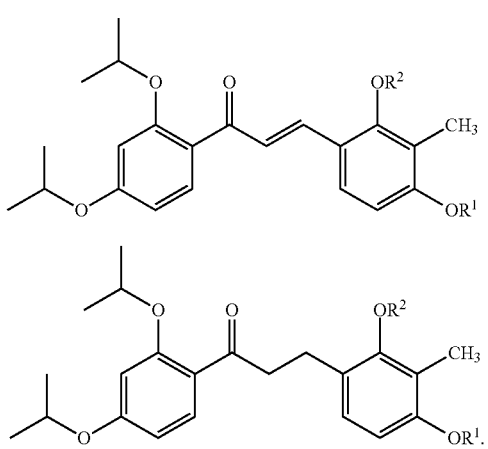

(IA-3)

(IB-3)

In other embodiments, each of $R^3$ and $R^4$ are hydrogen and the compound of structure (I) has one of the following structures (IA-4) or (IB-4):

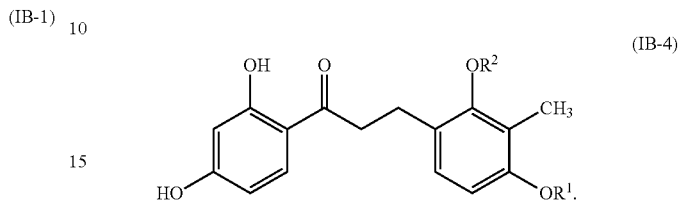

(IA-4)

(IB-4)

In certain other embodiments, $R^6$ is oxo, $R^5$ is hydrogen and the compound of structure (I) has one of the following structures (IC) or (ID):

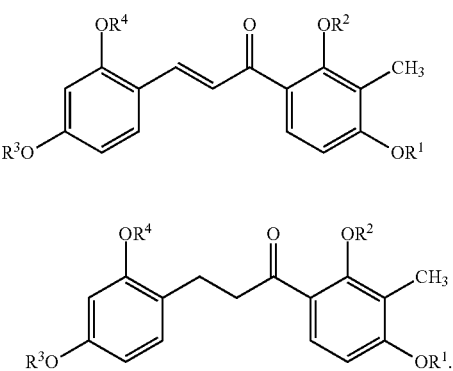

(IC)

(ID)

In some other embodiments, each of $R^1$ and $R^2$ are alkyl. For example, in some aspects each of $R^1$ and $R^2$ are methyl and the compound of structure (I) has one of the following structures (IC-1) or (ID-1):

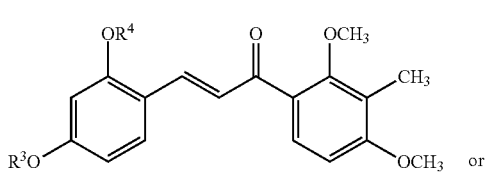

(IC-1)

(ID-1)

In yet other embodiments, each of $R^3$ and $R^4$ are aralkyl. For example, in some embodiments, $R^3$ and $R^4$ are benzyl and the compound of structure (I) has one of the following structures (IC-2) or (ID-2):

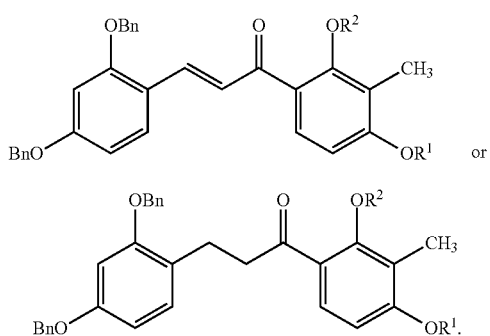
(IC-2)

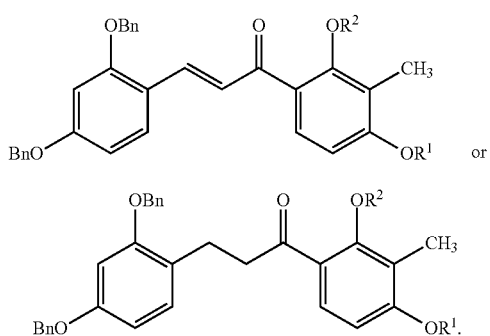
(IC-2)

In some other embodiments, each of $R^3$ and $R^4$ are alkyl. For example, in some aspects each of $R^3$ and $R^4$ are isopropyl and the compound of structure (I) has one of the following structures (IC-3) or (ID-3):

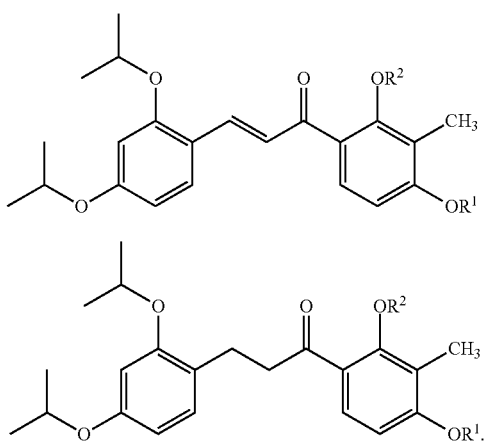
(IC-3)

or (IB-3)

In some other embodiments, each of $R^3$ and $R^4$ are hydrogen and the compound of structure (I) has one of the following structures (IC-4) or (ID-4):

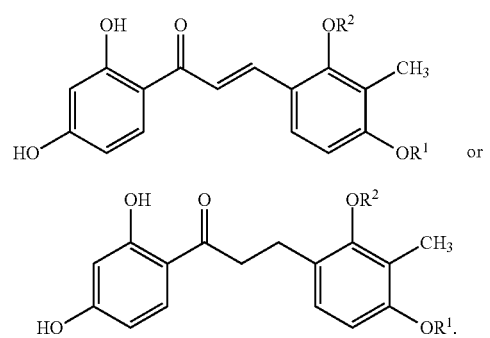
(IC-4)

or (ID-4)

In some other embodiments, at least one of $R^3$ or $R^4$ is allyl. For example, in some embodiments, each of $R^3$ and $R^4$ are allyl.

In some embodiments, at least one of $R^3$ or $R^4$ is alkyl. In certain other embodiments, at least one of $R^1$ or $R^2$ is methyl. For example, in some embodiments each of $R^1$ and $R^2$ is methyl.

In other embodiments, at least one of $R^3$ or $R^4$ is aralkyl.

In other embodiments, the compound of structure (I) has one of the following structures (IA-5), (IA-6), (IA-7) or (IA-8):

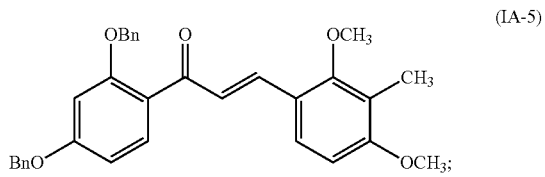
(IA-5)

(IA-6)

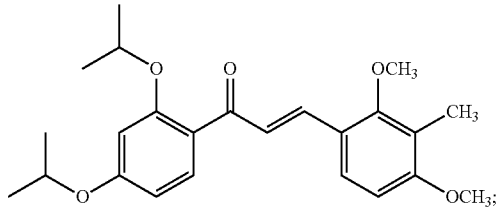
(IA-7)

or

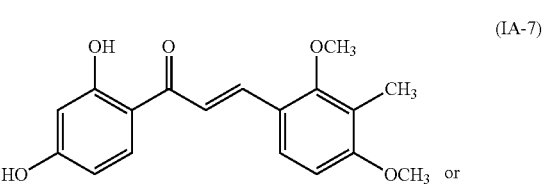
(IA-8)

In still other embodiments, the compound of Structure (I) has one of the following structures (IB-5), (IB-6), (IB-7) or (IB-8):

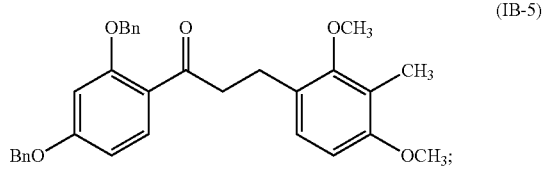
(IB-5)

(IB-6)

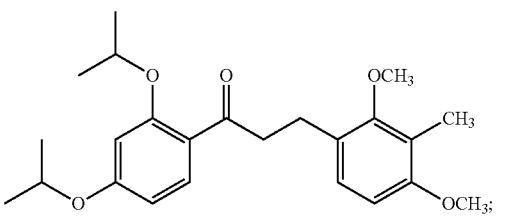

-continued (IB-7)
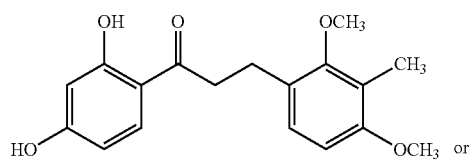

or (IB-8)
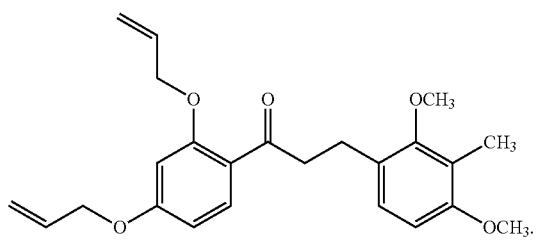

In yet other embodiments, the compound of structure (I) has one of the following structures (IC-5), (IC-6), (IC-7) or (IC-8):

(IC-5)
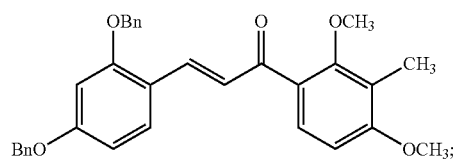

(IC-6)
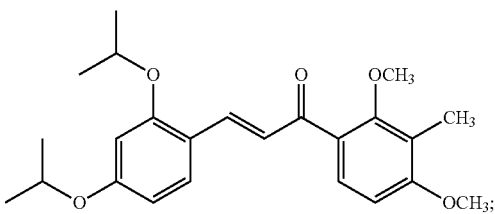

(IC-7)
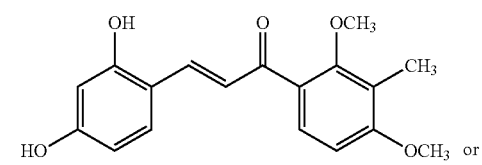

or (IC-8)
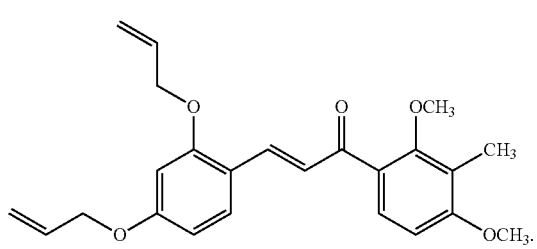

In still other embodiments, the compound of structure (I) has one of the following structures (ID-5), (ID-6), (ID-7) or (ID-8):

(ID-5)
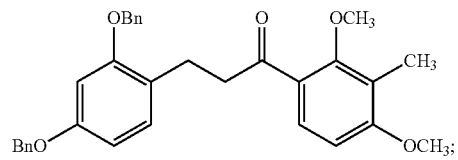

(ID-6)
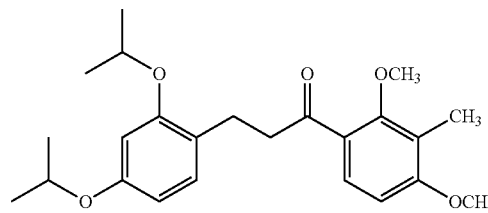

(ID-7)
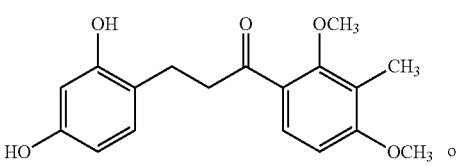

or (ID-8)
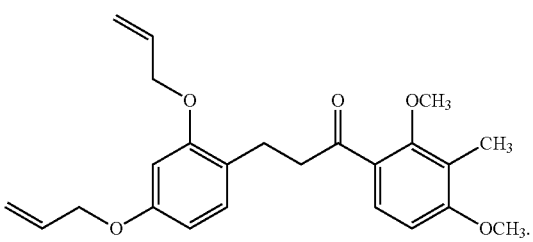

In yet other embodiments, at least one of $R^3$ or $R^4$ is allyl. For example, in some aspects each of $R^3$ and $R^4$ are allyl. In yet other embodiments, at least one of $R^3$ or $R^4$ is benzyl.

The present disclosure is also directed to a method for preparing a compound of structure (II):

(III)
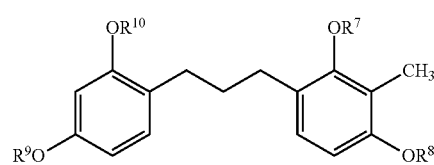

or a stereoisomer, tautomer or salt thereof, wherein:
$R^7$, $R^8$, $R^9$ and $R^{10}$ are each independently hydrogen, alkyl, aryl or aralkyl,
the method comprising reducing a compound of structure (I):

(I)
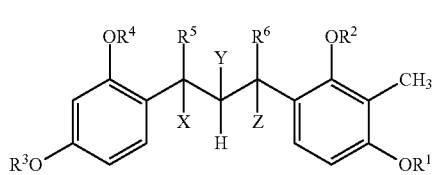

or a stereoisomer, tautomer or salt thereof, wherein:
$R^1$, $R^2$, $R^3$ and $R^4$ are each independently hydrogen, alkyl, aryl or aralkyl;

one of $R^5$ or $R^6$ is oxo, and the other of $R^5$ or $R^6$ is hydrogen; and

X, Y and Z are each independently absent or hydrogen, or X and Y or Z and Y may join to form a bond, wherein X, Y and Z are each chosen such that all valences are satisfied.

In some embodiments of the disclosed method, the compound of structure (I) has one of the following structures (IB) or (ID):

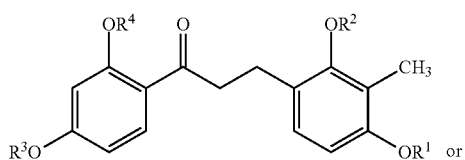
(IB)

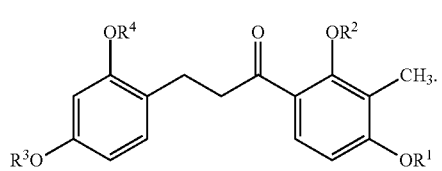
(ID)

In other embodiments of the disclosed method, each of $R^1$ and $R^2$ are methyl. In certain other embodiments, each of $R^3$ and $R^4$ are hydrogen. For example, in some aspects each of $R^1$ and $R^2$ are methyl, each of $R^3$ and $R^4$ are hydrogen and the compound of structure (I) has one of the following structures (IB-7) or (ID-7):

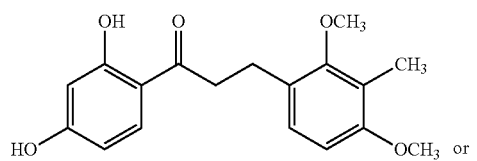
(IB-7)

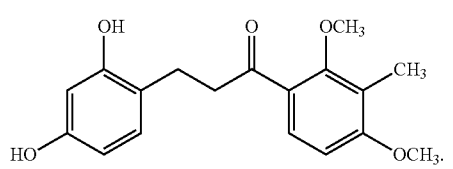
(ID-7)

In some embodiments of the disclosed method, reducing comprises treating a compound of structure (IB) or (ID) with sodium bis(2-methoxyethoxy)aluminum hydride, Raney nickel and hydrogen gas or zinc/HCl.

In certain other embodiments of the disclosed method, the compound of structure (IB) or (ID) has been prepared by reducing a compound of structure (IA) or (IC), respectively:

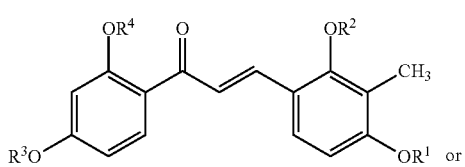
(IA)

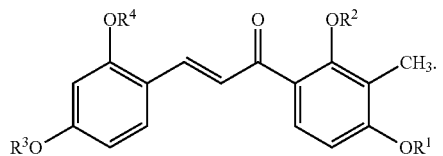
(IC)

For example, in some embodiments of the foregoing method, each of $R^1$ and $R^2$ are methyl, each of $R^3$ and $R^4$ are benzyl or each of $R^3$ and $R^4$ are isopropyl. For example, in some aspects, each of $R^1$ and $R^2$ are methyl, each of $R^3$ and $R^4$ are benzyl and the compound of structure (I) has one of the following structures (IA-5) or (IC-5):

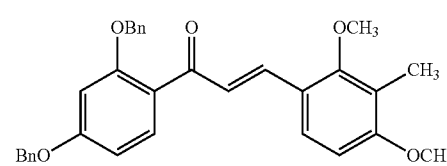
(IA-5)

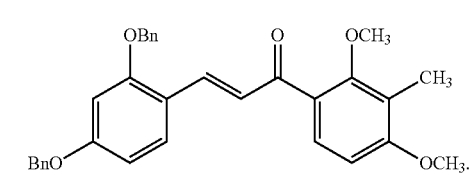
(IC-5)

In certain examples of the foregoing method, each of $R^1$ and $R^2$ are methyl, each of $R^3$ and $R^4$ are isopropyl and the compound of structure (I) has one of the following structures (IA-6) or (IC-6):

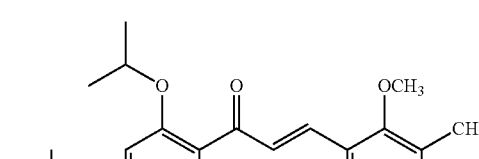
(IA-6)

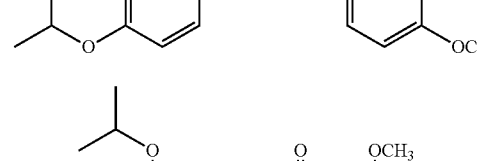
(IC-6)

In yet other embodiments, reducing comprises treating a compound of structure (IA) or (IC) with palladium on carbon and formic acid/$H_2$ (gas) or palladium on carbon and ammonium formate.

In certain other embodiments of the disclosed method, the compound of structure (I) has been prepared by reaction of a compound of structure (III) and a compound of structure (IV):

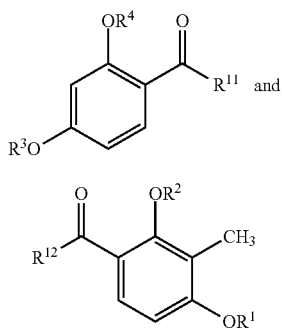

(III)

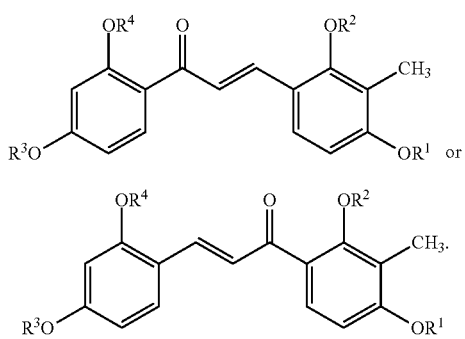

(IA)

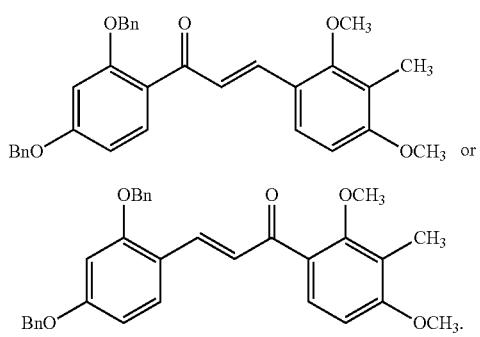

(IC)

or a stereoisomer, tautomer or salt thereof, wherein one of $R^{11}$ or $R^{12}$ is hydrogen and the other of $R^{11}$ or $R^{12}$ is methyl. For example, in some embodiments, $R^{11}$ is hydrogen and $R^{12}$ is methyl. In some other exemplary embodiments, $R^{11}$ is methyl and $R^{12}$ is hydrogen. In some embodiments, each of $R^1$ and $R^2$ are methyl, each of $R^3$ and $R^4$ are benzyl or each of $R^3$ and $R^4$ are isopropyl.

In yet other embodiments of the disclosed method, the compound of structure (I) has one of the following structures (IB) or (ID):

For example, in some embodiments of the foregoing method, each of $R^1$ and $R^2$ are methyl, each of $R^3$ and $R^4$ are benzyl or each of $R^3$ and $R^4$ are isopropyl. In certain other embodiments, each of $R^1$ and $R^2$ are methyl, each of $R^3$ and $R^4$ are benzyl and the compound of structure (I) has one of the following structures (IA-5) or (IC-5):

In some embodiments of the foregoing method, reducing comprises the steps of:

(a) treatment with palladium on carbon and formic acid/$H_2$ (gas) or palladium on carbon and ammonium formate; and
(b) treatment with sodium bis(2-methoxyethoxy)aluminum hydride, Raney nickel and hydrogen gas or zinc/HCl.

In yet other embodiments of the disclosed method, each of $R^1$ and $R^2$ are methyl, each of $R^3$ and $R^4$ are isopropyl and the compound of structure (I) has one of the following structures (IA-6) or (IC-6):

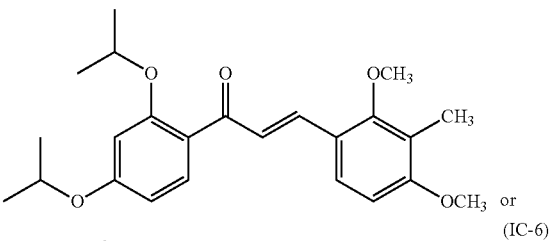

(IA-6)

or

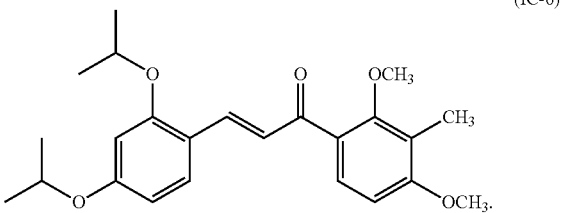

(IC-6)

In some embodiments of the foregoing method, reducing comprises treating a compound of structure (IA-6) or (IC-6) with palladium on carbon, hydrogen gas and acetic acid.

In yet other embodiments, the compound of structure (II) has the following structure (II-2):

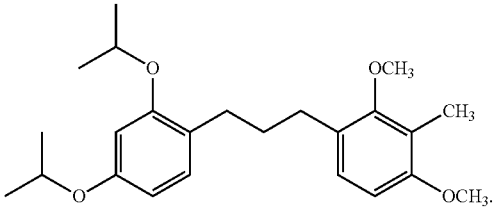

(II-2)

In still other embodiments, the compound of structure (II) has the following structure (II-1):

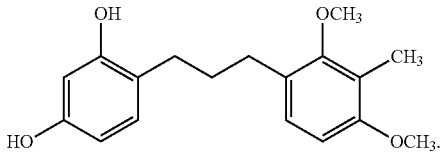

(II-1)

1. Preparation of 1,3-Diarylpropanes

A. Comparative Preparations of 1,3-diarylpropanes

Various reports have described the preparation of 1,3-diarylpropanes; however, none of the reported methods meet the criteria required for safe and cost-effective preparation of these compounds at large scales. For example, U.S. Pat. No. 5,880,314 describes the preparation of 1,3-bis(2,4-dihydroxyphenyl)propane by complete reduction of the corresponding chalcone. A small quantity (~6 grams) of the chalcone was treated with Raney nickel and hydrogen gas for an extended period of time (~20 hours), and an approximately 23% yield of purified 1,3-diarylpropane was obtained. Although preparation of 1,3-diarylpropanes was feasible via this method, the low yield and use of explosive mixtures of hydrogen gas and Raney nickel make this method unsuitable for large-scale production.

A one step reduction of Chalcones to 1,3-diarylpropanes has also been reported in J Braz. Chem. Soc, 1999, 10, 347-353. However, the disclosed method is not suitable for preparation of compounds of structure (II) because it results in a mixture of compounds which are difficult to separate. In addition, the disclosed methods suffer from a lack of reproducibility from batch to batch.

A one step reduction of chalcones to saturated alcohols with ammonium formate/Pd-Carbon has also been reported (Lett. In Org. Chem. 2006, 3, 39-41). However, this method does not include complete reduction to a 1,3-diarylpropane and does not address the deficiencies of other preparation methods.

B. Improved Preparation of 1,3-Diarylpropanes

As noted above, known compounds and methods are unsuitable for preparation of compounds of structure (II), particularly at large scales. The compounds and methods provided by the present disclosure address the problems previously associated with preparation of 1,3-diarylpropane compounds. Reduction of a novel chalcone compound (i.e., a compound of structure (I)) to the corresponding ketone, followed by complete reduction of the ketone, results in 1,3-diarylpropanes in high yield and purity. In addition, the compounds and methods of the present disclosure allow for safer operation and easier reagent handling than when other known compounds and methods are employed. Accordingly, this new approach is amenable to safe and cost-effective production of 1,3-diarylpropanes at scales not obtainable (e.g., pilot plant or larger) when compounds of structure (I) are not used.

Methods of the present disclosure include preparation of compounds of structure (II) via a two-step reduction of compounds of structure (I). In certain embodiments, the methods result in at least a 25% increased yield of 1,3-diarylpropane relative to other known methods. Accordingly, in some embodiments complete reduction of a compound of structure (I) yields at least 50%, at least 60%, at least 70%, at least 80%, at least 90%, at least 95% or at least 99% of the theoretical maximum of a compound of structure (II).

In addition to increased yield, the methods of the invention also provide for 1,3-diarylpropane compounds of higher purity than possible when other methods are employed. This high purity makes compounds of structure (II), prepared according to the present disclosure, easier to crystallize, thus increasing their purity even higher. Accordingly, in some embodiments compounds of structure (II) prepared according to the disclosed method have a purity of at least 95%, at least 96%, at least 97%, at least 98%, at least 99%, at least 99.5%, at least 99.9% or at least 99.99% as determined by HPLC.

The compounds of the present invention may be prepared by known organic synthesis techniques, including the methods described in more detail in the Examples. However in general, the compounds of structure (I) and (II) may be made by the following General Reaction Scheme (Scheme 1), wherein L is an appropriate leaving group (e.g., halogen), and the values for $R^1$-$R^{12}$, X, Y and Z are as defined above.

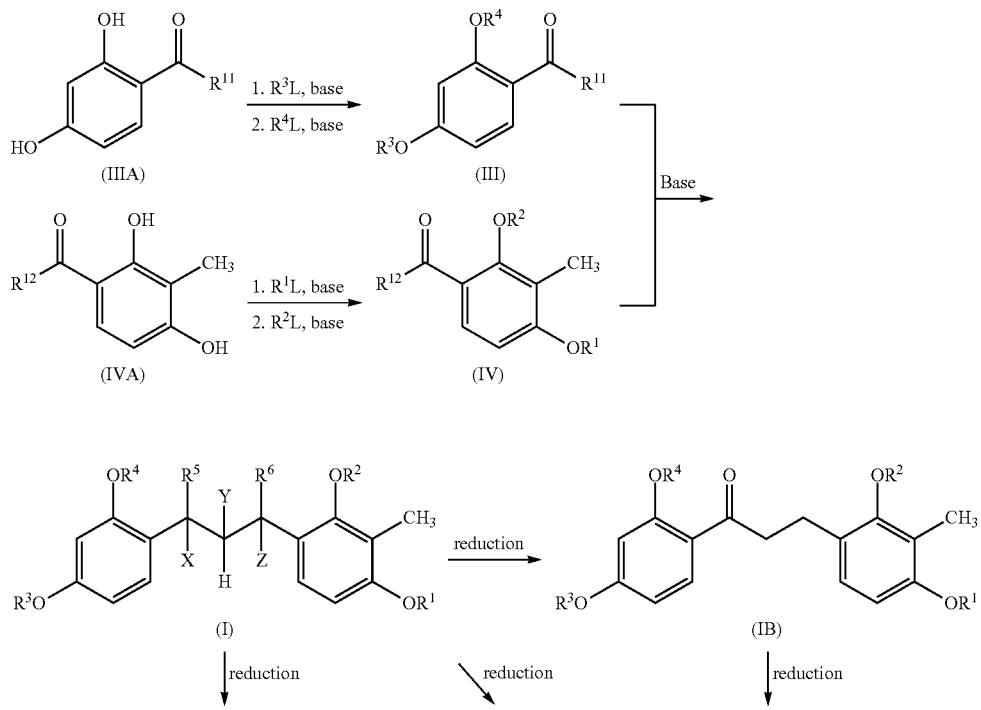

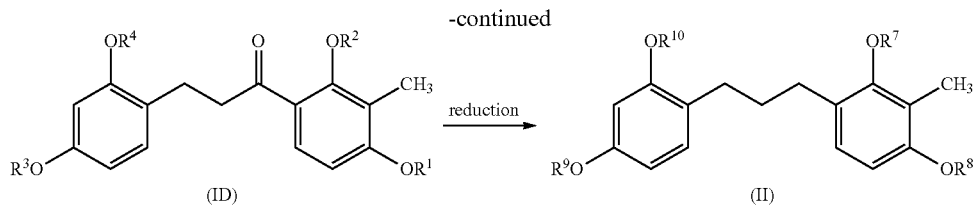

Referring to Scheme 1, compounds of structure (IIIA) can be purchased or prepared according to methods known in the art. Reaction of the phenolic hydroxyls with $R^3L$ under basic conditions (e.g., potassium or sodium carbonate) followed by reaction with $R^4L$ under basic conditions yields compounds of structure (III). In one specific example, $R^3$ and $R^4$ are each benzyl and $R^3L$ and $R^4L$ are each benzyl chloride. In another specific example, $R^3$ and $R^4$ are each isopropyl and $R^3L$ and $R^4L$ are each 2-bromopropane. One skilled in the art will recognize that when $R^3=R^4$, both groups can be added in a single step. In addition, the order of reaction may be reversed, and or appropriate protecting groups employed to obtain the desired compound of structure (III).

In a similar manner, compounds of structure (IVA) can be reacted with $R^1L$ followed by $R^2L$ under basic conditions to yield compounds of structure (IV). In one specific example, $R^1$ and $R^2$ are each methyl and $R^1L$ and $R^2L$ are each an appropriate methylating reagent (e.g., methyl iodide, etc.). Again, in certain embodiments wherein $R^1=R^2$ only one step may be required and variations to the order of reaction and protecting group schemes are possible.

Aldol condensation of compounds of structure (III) with compounds of structure (IV) under basic conditions then yields compounds of structure (I). In this context, various conditions may be employed in practicing the disclosed method. For example, reagents such as NaH, KOH, NaOH, LiOH, NaOMe, t-BuOK and the like may be employed to perform the aldol condensation. In certain embodiments, KOH in a solvent such as methanol may be used.

Compounds of structure (I) wherein $R^5$ is oxo and Y and Z form a bond can be reduced to form compounds of structure (IB). Appropriate reduction conditions include conditions known in the art for reduction of the alkene bond in alpha-beta unsaturated carbonyl compounds. Such conditions include, but are not limited to, hydrogenation in the presence of an appropriate catalyst (e.g., palladium on carbon) and a hydrogen source such as hydrogen gas, formic acid, ammonium formate, cyclohexa-1,4-diene and other reagents capable of donating a hydrogen atom. In certain embodiments, transfer hydrogenation conditions (e.g., a catalyst and a hydrogen atom donor such as ammonium formate or formic acid) are particularly useful as such conditions can be safer, and in certain examples the reagents may be easier to handle than hydrogen gas, especially at large scales. In one specific example, the reduction conditions comprise a palladium catalyst (e.g., Pd/C) and ammonium formate. In other examples, the reaction conditions comprise a palladium catalyst (e.g., Pd/C) and formic acid and/or hydrogen gas. Other exemplary reagents for transfer hydrogenation include $(Ph_3P)RhCl$-EtSiH-Bz, $NaBH_4$-pyridine, $NaBH_4$—$NiCl_2$-Dioxane-MeOH (see e.g., J. Chem. Res. 2006, 584-585). Alternatively, compounds of structure (ID) can be prepared under similar conditions by reduction of compounds of structure (I) wherein $R^6$ is oxo and X and Y form a bond.

Compounds of structure (II) can be prepared by complete reduction of the carbonyl group of compounds of structure (IB) or (ID) under appropriate conditions. Reduction conditions in this context include, but are not limited to, hydrogenation in the presence of an appropriate catalyst (e.g., Pd/C, Raney nickel and the like) and hydrogen gas. Other reduction conditions include treatment with zinc/HCl or Vitride® (i.e., sodium bis(2-methoxyethoxy)aluminum hydride) or other hydride reagents. In one specific example, the reduction conditions comprise treatment with Vitride®. In another example, reduction comprises treatment with Raney Ni/$H_2$ and Zn/HCl. Other reduction conditions are well known to those skilled in the art.

Alternatively, compounds of structure (II) can be prepared in a one-step reduction of compounds of structure (I). Appropriate conditions in this context include treatment of compounds of structure (I) with an appropriate catalyst (e.g., palladium on carbon) and hydrogen gas. In some embodiments, an acid, such as acetic acid may also be used in addition to a catalyst and hydrogen gas. In other embodiments, transfer hydrogenation conditions may be employed. In some examples of a one-step reduction of compounds of structure (I) to compounds of structure (II), at least one of $R^3$ or $R^4$ is isopropyl. For example, each of $R^3$ and $R^4$ may be isopropyl.

One skilled in the art will recognize that variations to the exact steps and reagents outlined in Scheme 1 are possible. In addition, protecting groups may be utilized in the preparation of the disclosed compounds. For example, in certain embodiments, the values of $R^1$, $R^2$, $R^3$ or $R^4$ are chosen such that a protected hydroxyl group results. In particular embodiments, $R^3$ and $R^4$ are hydroxyl protecting groups that can be removed to reveal a free phenol. Protecting groups useful in this context include protecting groups that can be removed by hydrogenation or under acidic, basic or other selective conditions. For example, alkyl (e.g., isopropyl, allyl and the like), aryl, aralkyl (e.g., benzyl, trityl and the like), are all useful hydroxyl protecting groups which may be employed in the context of the current disclosure.

In one particular embodiment, one or both of $R^3$ and $R^4$ are protecting groups which can be removed by hydrogenation, for example, benzyl groups. In other embodiments, one or both of $R^3$ and $R^4$ are isopropyl. Isopropyl can be selectively removed by treatment with $AlCl_3$ or other Lewis acids (J. Org. Chem. 1998, 64, 9139). Advantages of using isopropyl as a protecting group within the context of the present disclosure include: 1) low molecular weight compared to other protecting groups so there is less mass loss; when the protecting group is removed 2) the isopropyl compound is soluble in methanol; 3) one step reduction to 1,3-diarylpropane is possible so expensive vitride reduction step can be avoided; and 4) selective deprotection of the isopropyl group proceeds in high yield. The protecting groups can be removed during one of the above described reaction steps (e.g., benzyl groups may be removed during the hydrogenation of the alkene bond) or additional steps may added to the above scheme to remove the protecting groups. Such additional steps may include treatment with $AlCl_3$ or other appropriate reagent. Other protecting groups useful within the context of the present disclosure are well known to those of skill in the art, for example, those found in "Greene's Protective Groups in Organic Synthesis", 4th Edition, Peter G. M. Wuts and Theodora W. Greene, October 2006 which is hereby incorporated by reference in its entirety.

Compounds of the present disclosure can be purified using known purification techniques. Such techniques include, but are not limited to, chromatography (e.g., HPLC, column chromatography, TLC, etc.), trituration, extraction, salt formation, crystallization, etc. In certain embodiments, crystallization techniques are employed for purification of compounds of structure (I) or (II). Such techniques are especially useful at large scale where other purification techniques are not feasible.

The compounds of the present invention may generally be utilized as the free acid (e.g., phenol) or free base. Alternatively, the compounds of this invention may be used in the form of acid or base addition salts. Acid addition salts of amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts include those salts that form with a phenol or enol anion or with other acidic moieties and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "salt" of structure (I) or structure (II) is intended to encompass any and all acceptable salt forms.

With regard to stereoisomers, the compounds of structure (I) or (II) may have chiral centers and may occur as racemates, enantiomerically enriched mixtures and as individual enantiomers or diastereomers. For ease of representation, the compounds of structure (I) are depicted in a trans configuration; however, the compounds of structure (I) may exist as E or Z isomers (i.e., cis or trans). All such isomeric forms are included within the present invention, including mixtures thereof. Compounds of structure (I) or (II) may also possess axial chirality which may result in atropisomers. Furthermore, some of the crystalline forms of the compounds of structure (I) or (II) may exist as polymorphs, which are included in the present invention. In addition, some of the compounds of structure (I) or (II) may also form solvates with water or other organic solvents. Such solvates are similarly included within the scope of this invention.

The compounds of the present disclosure may also exist in different tautomeric forms or as mixtures of tautomers. Tautomers are compounds that result from the formal migration of a hydrogen atom accompanied by a switch of a single bond and adjacent double bond. For example, the enol and keto form of a compound are tautomers of each other. Tautomers within the context of the present disclosure include, but are not limited to, the following tautomeric pairs (IB) and (IB-T) and (ID) and (ID-T):

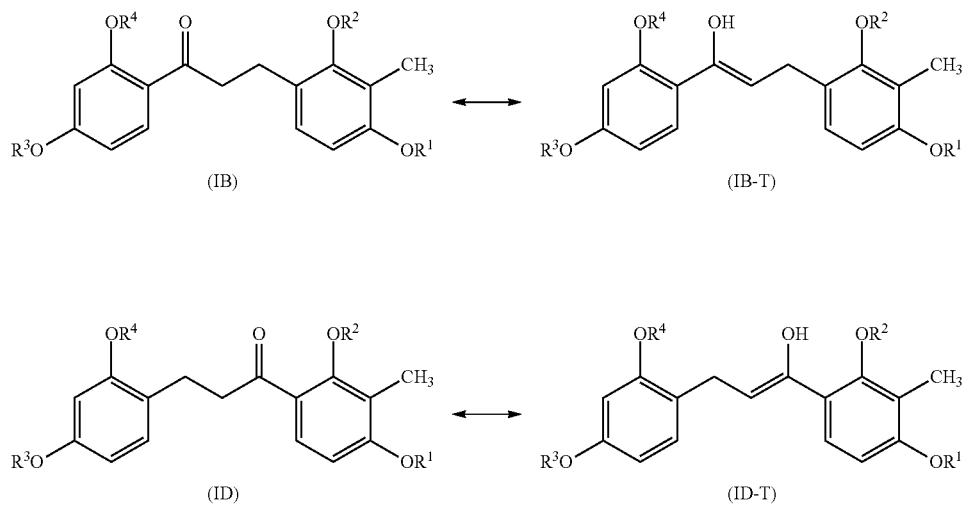

Representative compounds of this invention include (but are not limited to) the compounds listed in Table 1 below.

TABLE 1

Representative Compounds

| Cmp. # | Structure | Name |
|---|---|---|
| (IA-5) | 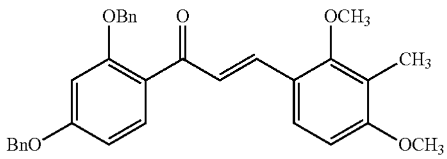 [SMILES: COc1ccc(/C=C/C(=O)c2ccc(OCc3ccccc3)cc2OCc2ccccc2)c(OC)c1C] | (E)-1-(2,4-bis(benzyloxy)phenyl)-3-(2,4-dimethoxy-3-methylphenyl)prop-2-en-1-one |
| (IA-6) | 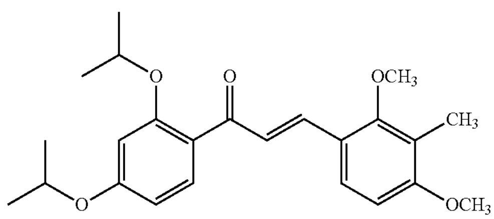 [SMILES: COc1ccc(/C=C/C(=O)c2ccc(OC(C)C)cc2OC(C)C)c(OC)c1C] | (E)-1-(2,4-diisopropoxyphenyl)-3-(2,4-dimethoxy-3-methylphenyl)prop-2-en-1-one |
| (IA-7) | 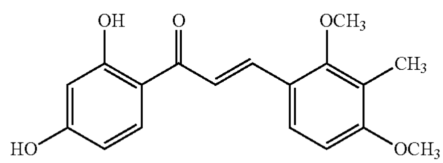 [SMILES: COc1ccc(/C=C/C(=O)c2ccc(O)cc2O)c(OC)c1C] | (E)-1-(2,4-dihydroxyphenyl)-3-(2,4-dimethoxy-3-methylphenyl)prop-2-en-1-one |
| (IA-8) | 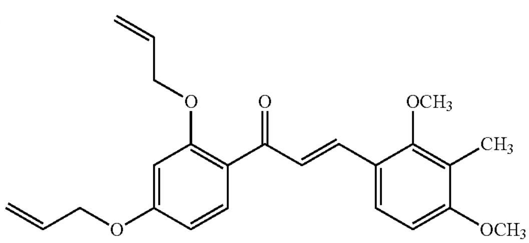 [SMILES: C=CCOc1ccc(C(=O)/C=C/c2ccc(OC)c(C)c2OC)c(OCC=C)c1] | (E)-1-(2,4-bis(allyloxy)phenyl)-3-(2,4-dimethoxy-3-methylphenyl)prop-2-en-1-one |
| (IB-5) | 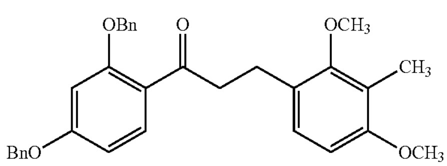 [SMILES: COc1ccc(CCC(=O)c2ccc(OCc3ccccc3)cc2OCc2ccccc2)c(OC)c1C] | 1-(2,4-bis(benzyloxy)phenyl)-3-(2,4-dimethoxy-3-methylphenyl)propan-1-one |
| (IB-6) | 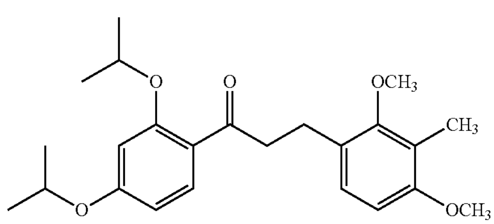 [SMILES: COc1ccc(CCC(=O)c2ccc(OC(C)C)cc2OC(C)C)c(OC)c1C] | 1-(2,4-diisopropoxyphenyl)-3-(2,4-dimethoxy-3-methylphenyl)propan-1-one |
| (IB-7) | 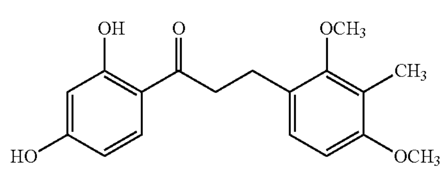 [SMILES: COc1ccc(CCC(=O)c2ccc(O)cc2O)c(OC)c1C] | 1-(2,4-dihydroxyphenyl)-3-(2,4-dimethoxy-3-methylphenyl)propan-1-one |

TABLE 1-continued

Representative Compounds

| Cmp. # | Structure | Name |
|---|---|---|
| (IB-8) | 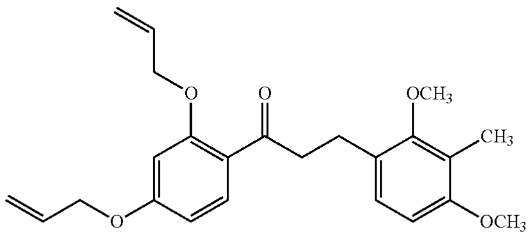 [SMILES: C=CCOc1ccc(C(=O)CCc2ccc(OC)c(C)c2OC)c(OCC=C)c1] | 1-(2,4-bis(allyloxy)phenyl)-3-(2,4-dimethoxy-3-methylphenyl)propan-1-one |
| (IC-5) | 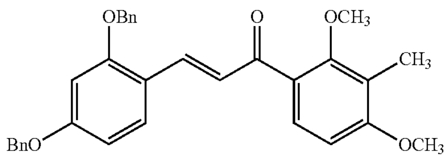 [SMILES: COc1ccc(C(=O)/C=C/c2ccc(OCc3ccccc3)cc2OCc2ccccc2)c(OC)c1C] | (E)-3-(2,4-bis(benzyloxy)phenyl)-1-(2,4-dimethoxy-3-methylphenyl)prop-2-en-1-one |
| (IC-6) | 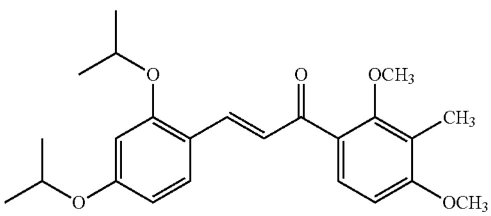 | (E)-3-(2,4-diisopropoxyphenyl)-1-(2,4-dimethoxy-3-methylphenyl)prop-2-en-1-one |
| (IC-7) | 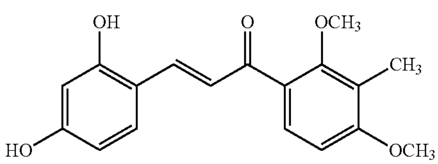 [SMILES: COc1ccc(C(=O)/C=C/c2ccc(O)cc2O)c(OC)c1C] | (E)-3-(2,4-dihydroxyphenyl)-1-(2,4-dimethoxy-3-methylphenyl)prop-2-en-1-one |
| (IC-8) | 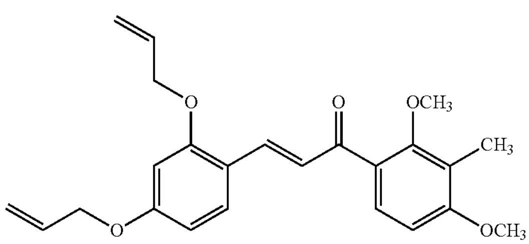 [SMILES: C=CCOc1ccc(/C=C/C(=O)c2ccc(OC)c(C)c2OC)c(OCC=C)c1] | (E)-3-(2,4-bis(allyloxy)phenyl)-1-(2,4-dimethoxy-3-methylphenyl)prop-2-en-1-one |
| (ID-5) | 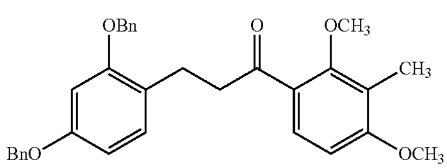 [SMILES: COc1ccc(C(=O)CCc2ccc(OCc3ccccc3)cc2OCc2ccccc2)c(OC)c1C] | 3-(2,4-bis(benzyloxy)phenyl)-1-(2,4-dimethoxy-3-methylphenyl)propan-1-one |
| (ID-6) | 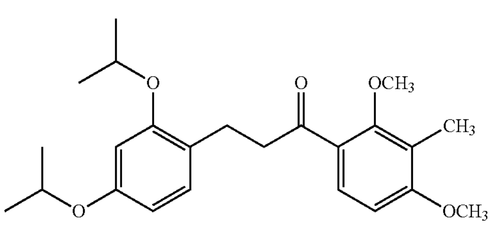 [SMILES: COc1ccc(C(=O)CCc2ccc(OC(C)C)cc2OC(C)C)c(OC)c1C] | 3-(2,4-(diisopropoxyphenyl)-1-(2,4-dimethoxy-3-methylphenyl)propan-1-one |

TABLE 1-continued

Representative Compounds

| Cmp. # | Structure | Name |
|---|---|---|
| (ID-7) | 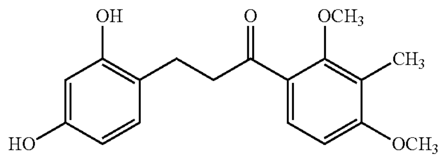 [SMILES: COc1ccc(C(=O)CCc2ccc(O)cc2O)c(OC)c1C] | 3-(2,4-dihydroxyphenyl)-1-(2,4-dimethoxy-3-methylphenyl)propan-1-one |
| (ID-8) | 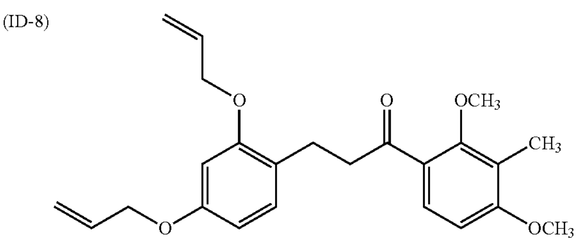 | 3-(2,4-bis(allyloxy)phenyl)-1-(2,4-dimethoxy-3-methylphenyl)propan-1-one |
| (II-1) | 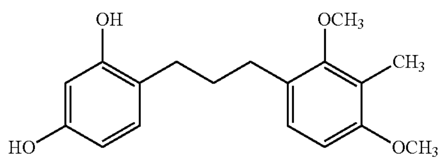 [SMILES: COc1ccc(CCCc2ccc(O)cc2O)c(OC)c1C] | 3-(2,4-bis(allyloxy)phenyl)-1-(2,4-dimethoxy-3-methylphenyl)propan-1-one |
| (II-2) | 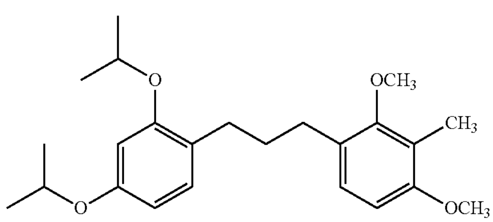 [SMILES: COc1ccc(CCCc2ccc(OC(C)C)cc2OC(C)C)c(OC)c1C] | 1-(3-(2,4-diisopropoxyphenyl)propyl)-2,4-dimethoxy-3-methylbenzene |

The following examples are provided for purposes of illustration, not limitation.

EXAMPLES

Certain compounds of the present disclosure may be prepared according to the following schemes and the knowledge of one skilled in the art. All temperatures are in degrees Celsius (° C.) unless otherwise indicated. All of the synthesized compounds were characterized by at least proton $^1$H NMR, $^{13}$C NMR and LC/MS. During work up of reactions, the organic extract was dried over sodium sulfate ($Na_2SO_4$), unless mentioned otherwise. The following abbreviations are used for the commonly employed reagents: $Na_2SO_4$ (sodium sulfate), HCl (hydrochloric acid), NaOH (sodium hydroxide), KOH (potassium hydroxide), NaCl (sodium chloride), Pd—C (palladium on carbon), $K_2CO_3$ (potassium carbonate), $NaHCO_3$ (sodium bicarbonate), BnCl (Benzylchloride), DMF (Dimethyl Formamide) and RT (room temperature).

Example 1

Synthesis of 1-(2,4-bis(benzyloxy)phenyl)ethanone

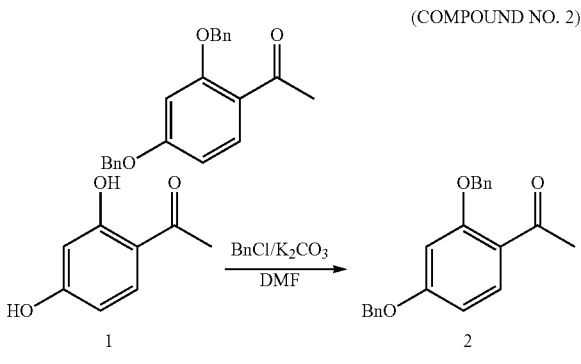

To a mixture of 2,4-dihydroxyacetophenone 1 (1.00 equiv. 24 kg) and potassium carbonate (2.9 equiv. 63.3 kg) in dry DMF (235 L), benzylchloride (2.5 equiv., 50 kg) was added over 1 h at room temperature (25° C.). The reaction mixture was then heated to about 85-90° C. for ~14 h and held at this temperature until found complete by HPLC. After completion, the reaction mixture was allowed to cool to room temperature (25° C.) and filtered through a bed of Celite®. The Celite® bed was washed with acetone (3 volumes), and the combined filtrate was concentrated in vacuo to a dry solid. This solid was dissolved in ethyl acetate (5 volumes) and washed with sodium bicarbonate solution (2×5 volumes) followed by brine (3 volumes). The ethyl acetate layer was then dried with sodium sulfate (75 kg), filtered and concentrated by evaporation to dryness. The residue was triturated with hexane (100 L) and filtered. This residue was then washed with hexane (35 L) and dried at 35-40° C. to a constant weight to obtain compound 2 (40 Kg) 77%. MP: 83.1° C.; $^1$H-NMR (CDCl$_3$, 500 MHz): δ 7.86 (d, 1H, J=9 Hz), 7.55-7.41 (m, 8H), 7.40-7.36 (m, 2H), 6.65-6.63 (m, 1H), 6.62 (s, 1H), 5.13 (s, 2H), 5.10 (s, 2H), 2.57 (s, 3H); $^{13}$C-NMR (CDCl$_3$, 125 MHz): δ 197.762 (C), 169.511 (C), 160.106 (C), 136.190 (C), 136.019 (C), 132.729 (CH), 128.890 (CH), 128.724 (2CH), 128.568 (CH), 128.405 (CH), 128.298 (CH), 128.283 (CH), 127.635 (CH), 127.539 (CH), 121.779 (C), 106.325 (CH), 100.369 (CH), 70.753 (CH$_2$), 70.279 (CH$_2$), 32.145 (CH$_3$).

Example 2

Synthesis of (E)-1-(2,4-bis(benzyloxy)phenyl)-3-(2,4-dimethoxy-3-methylphenyl)prop-2-en-1-one

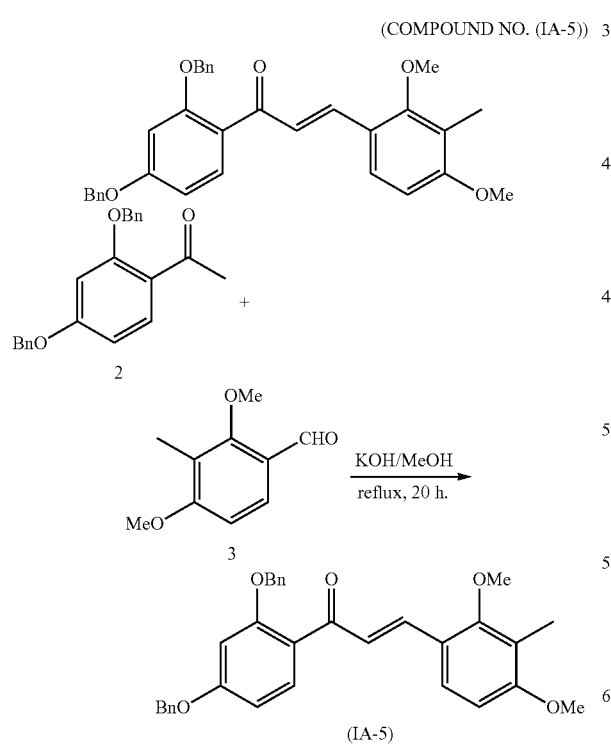

A solution of compound 2 (1.00 equiv., 40 kg) in MeOH (360 L) was cooled to 10-15° C. and treated with potassium hydroxide (5 equiv., 36 kg) in MeOH (360 L) over a period of 1.5 h. Next 2,4-dimethoxy-3-methylbenzaldehyde 3 (1.2 equiv., 25 kg) was added to the reaction mixture over 1.5 h while maintaining the temperature at 10-15° C. After the addition was complete, the reaction mixture was heated to 60-65° C. with stirring and held at this temperature until found complete by HPLC (~20 h). After completion, the reaction mixture was cooled back down to 10-15° C. and quenched with 2N aqueous HCl (13.5 L) to pH 2. The solid formed at this stage was filtered, washed with water and dissolved in acetic acid (360 L). This mixture was then cooled to 22-25° C. and stirred for 20 min upon which a yellow crystalline solid formed. The solid was collected by filtration, washed with water and dried under vacuum to a constant weight at 30° C. to obtain (IA-5) (50 Kg, 84%. MP: 125.1° C.; $^1$H-NMR (CDCl$_3$, 500 MHz): δ 7.93 (d, 1H, J=16 Hz), 7.83 (d, 1H, J=8.5 Hz), 7.54 (d, 1H, J=16 Hz), 7.46-7.43 (m, 5H), 7.42-7.40 (m, 1H), 7.39-7.37 (m, 1H), 7.32-7.30 (m, 3H), 7.15 (d, 1H, J=8.5 Hz), 6.69-6.67 (m, 2H), 6.53 (d, 1H, J=8.5 Hz), 5.13 (s, 2H), 5.12 (s, 2H), 3.87 (s, 3H), 3.69 (s, 3H), 2.15 (s, 3H); $^{13}$C-NMR (CDCl$_3$, 125 MHz): δ 190.599 (C), 162.977 (C), 160.380 (C), 159.365 (C), 159.080 (C), 137.633 (CH), 136.312 (C), 136.201 (C), 133.006 (CH), 128.246 (CH), 127.968 (CH), 127.576 (CH), 126.155 (CH), 125.970 (CH), 123.071 (C), 121.583 (C), 120.036 (C), 106.503 (CH), 100.706 (CH), 70.786 (CH$_2$), 70.290 (CH$_2$), 61.602 (CH$_3$), 55.691 (CH$_3$), 8.858 (CH$_3$).

Example 3

Synthesis of 1-(2,4-dihydroxyphenyl)-3-(2,4-dimethoxy-3-methylphenyl)propan-1-one

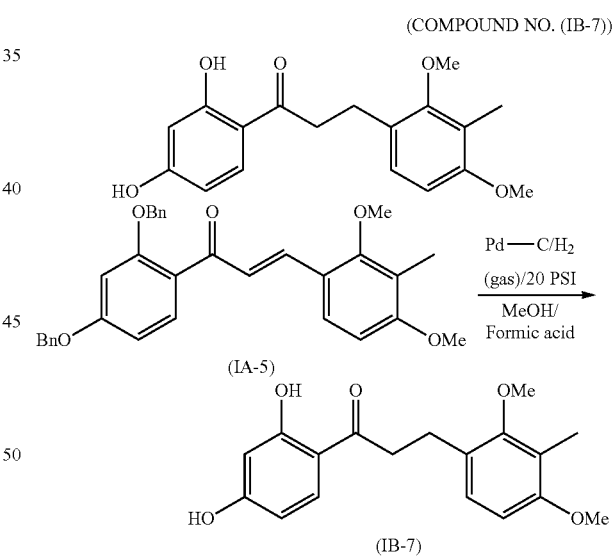

A solution of (IA-5) (1 equiv. 50 kg) in methanol (250 L) was treated with 10% Pd—C (10% by weight) and formic acid (250 L) and hydrogenated at 23-25° C. for 10 h. After the reaction was found complete by HPLC, the reaction mixture was filtered through Celite®. The Celite® bed was washed with ethyl acetate (40 L), and the combined filtrate was concentrated under vacuum at 35-40° C. to dryness. The residue was dissolved in ethyl acetate (3 volumes), washed with saturated sodium bicarbonate solution (20 L) until a pH of 7-7.5 was obtained. The ethyl acetate layer was then further washed with water (150 L) followed by brine. The ethyl acetate layer was then dried with sodium sulfate (88 kg), filtered and concentrated under vacuum at 35-45° C. to a constant weight to yield the product (25 Kg, 78%). MP: 171.0° C.; $^1$H-NMR (CDCl$_3$, 500 MHz): δ 12.79 (s, 1H), 7.69 (d, 1H, J=8.5 Hz), 7.02 (d, 1H, J=8.5 Hz), 6.61 (d, 1H, J=8.5 Hz), 6.38-6.34 (m, 2H), 5.63 (s, 1H), 3.82 (s, 3H), 3.76 (s, 3H), 3.20 (t, 2H, J=8 Hz), 2.99 (t, 2H, J=8 Hz), 2.18 (s, 3H); $^{13}$C-NMR (CDCl$_3$, 125 MHz): δ 204.899 (C), 165.218 (C), 162.323 (C), 157.592 (C), 157.359 (C), 132.425 (CH), 127.047 (CH), 125.688 (C), 119.917 (C), 113.910 (C), 107.561 (CH), 106.255 (CH), 103.508 (CH), 60.658 (CH$_3$), 55.657 (CH$_3$), 39.355 (CH$_2$), 25.423 (CH$_2$), 9.195 (CH$_3$).

Example 4

Synthesis of 4-(3-(2,4-dimethoxy-3-methylphenyl)propyl)benzene-1,3-diol

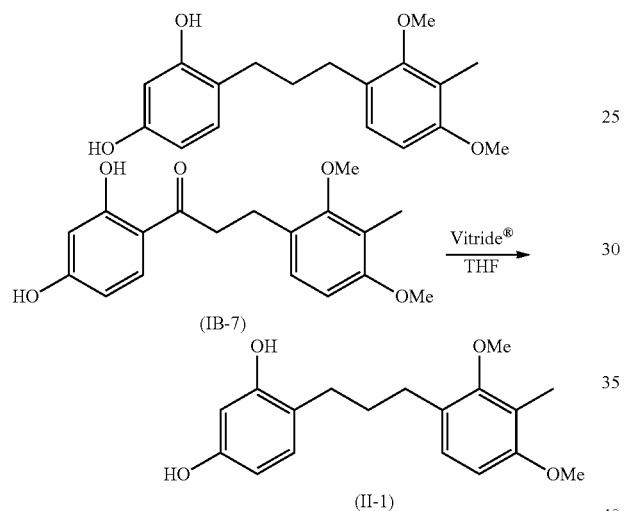

(COMPOUND NO. (II-1))

Under a nitrogen atmosphere, (IB-7) (1 equiv., 25 kg) was added into a reaction vessel containing THF (250 L) while stirring. The reaction mixture was then cooled to 0-5° C. and charged with Vitride® (i.e., sodium bis(2-methoxyethoxy) aluminum hydride, 1 equiv., 120 L) over 2.5 h. The reaction mixture was then heated and maintained at reflux until found complete by HPLC (~16 h). Next, the reaction was cooled to 0-5° C., quenched with 150 L of concentrated HCl (30-36%) in water (150 L) and stirred for 30 min. The reaction mixture was then diluted with water (150 L) and extracted twice with ethyl acetate (450 L and 375 L). The combined ethyl acetate extract was washed with aqueous sodium bicarbonate (25 kg in 150 L of water) followed by saturated sodium chloride (150 L). Charcoal (3.25 Kg) was added to the organic layer and the mixture was refluxed for 20 minutes. This mixture was filtered through Celite® and washed with ethyl acetate (20 L). The ethyl acetate layer was then dried with anhydrous sodium sulfate (25 kg) and concentrated under vacuum at 40-45° C. The crude product thus obtained was triturated for 4 h with toluene (5 L) at room temperature and filtered. This residue was washed with toluene (16 L), and the solid thus obtained was dried under vacuum for 8 h at 55-60° C. to produce 16.9 Kg of crude product.

The crude product (16.9 Kg) from the previous stage was dissolved in acetone (4 L) with heating to 55° C. This solution was then cooled to room temperature (24° C.) and treated with water (60 L) while stirring. Stirring was continued for 10 h at room temperature before the resulting solids were allowed to settle to the bottom, and the top organic layer was carefully removed. The remaining mixture was then diluted with petroleum ether (13 L), stirred for an additional 5 h at room temperature, filtered and then dried under vacuum for 12 h at 60° C. Product from two such crystallizations was combined, dried, ground and sieved to obtain purified (II-1) (15.64 Kg, 93%). MP: 108.0° C.; $^1$H-NMR (CDCl$_3$, 500 MHz): δ 6.96 (d, 1H, J=8.3 Hz), 6.85 (d, 1H, J=8.3 Hz), 6.62 (d, 1H, J=8.3 Hz), 6.27 (d, 1H, J=2.2 Hz), 6.21 (dd, 1H, J=2.2 Hz), 3.77 (s, 3H), 3.63 (s, 3H), 2.52-2.58 (m, 4H), 2.10 (s, 3H), 1.78-1.82 (m, 2H); $^{13}$C-NMR (CDCl$_3$, 125 MHz): δ 158.55 (C), 158.43 (C), 157.38 (C), 157.15 (C), 131.53 (CH), 128.95 (C), 128.28 (CH), 121.45 (C), 120.30 (C), 107.40 (CH), 103.60 (CH), 61.44 (CH$_3$), 56.19 (CH$_3$), 32.90 (CH$_2$), 30.77 (CH$_2$), 30.51 (CH$_2$), 9.195 (CH$_3$).

Example 5

Synthesis of 2,4-bis(benzyloxy)benzaldehyde

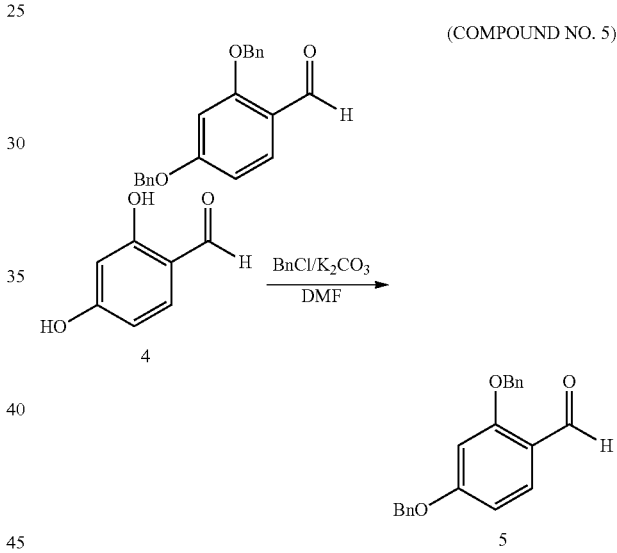

(COMPOUND NO. 5)

Using a procedure analogous to that described in Example 1, compound 4 is treated with benzyl chloride to obtain benzyl ether 5. Protecting groups are employed as needed.

Example 6

Synthesis of (E)-3-(2,4-bis(benzyloxy)phenyl)-1-(2,4-dimethoxy-3-methylphenyl)prop-2-en-1-one

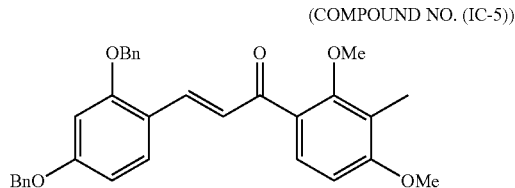

(COMPOUND NO. (IC-5))

-continued

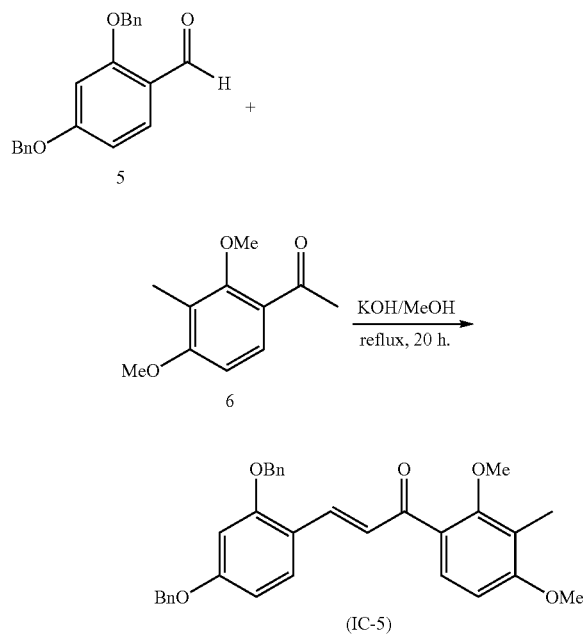

In a manner analogous to that described in Example 2, compounds 5 and 6 are treated under basic conditions to yield chalcone (IC-5).

Example 7

Synthesis of 3-(2,4-dihydroxyphenyl)-1-(2,4-dimethoxy-3-methylphenyl)propan-1-one

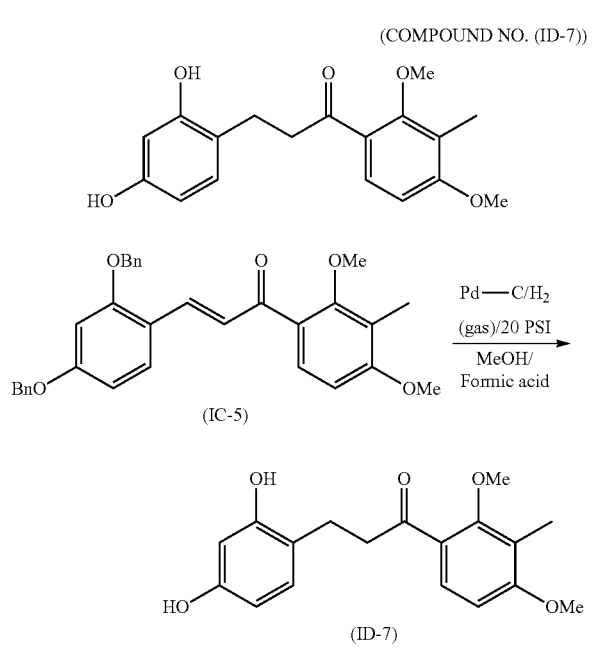

In a manner similar to that described in Example 3, compound (IC-5) is reduced to yield (ID-7).

Example 8

Synthesis of 4-(3-(2,4-dimethoxy-3-methylphenyl)propyl)benzene-1,3-diol

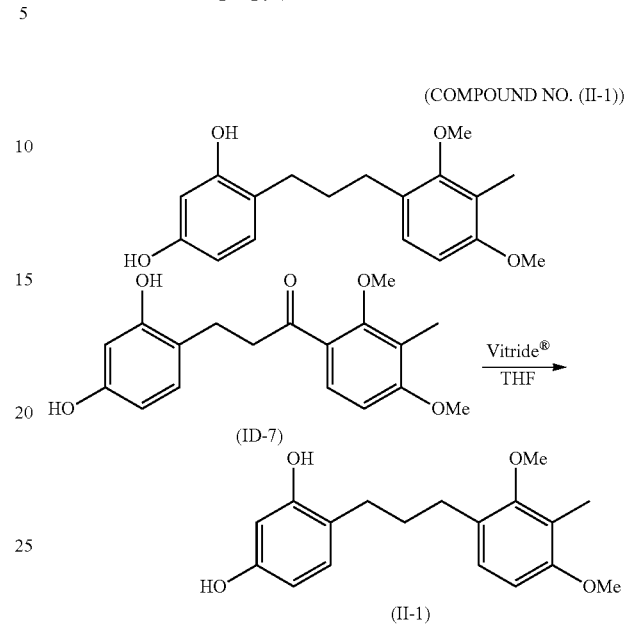

Compound (II-1) is prepared and purified in a manner analogous to that described in Example 4.

Example 9

Synthesis of 1-(2,4-diisopropoxyphenyl)ethanone

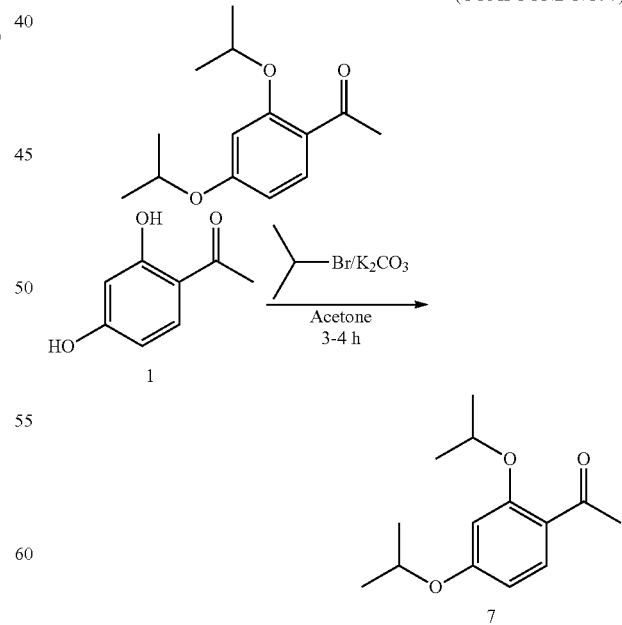

To a mixture of 2,4-dihydroxyacetophenone 1 (60.8 g, 0.4 mol) and potassium carbonate (160 g, 1.16 mol) in dry acetone (400 ml), isopropyl bromide (123 g, 1 mol) was added over 1 h at room temperature (25° C.). The reaction mixture was then refluxed for 4 h and monitored by TLC. After completion, the reaction mixture was allowed to cool to room temperature (25° C.) and filtered through a bed of celite. The celite bed was washed with acetone (3×100 ml) and the combined filtrate was concentrated down to dry solid. This solid was dissolved in ethyl acetate (500 ml), and the ethyl acetate was washed sequentially with 5% HCl (200 ml), sodium bicarbonate (2×200 ml) and brine solution (200 ml). The ethyl acetate layer was then dried over sodium sulfate, filtered and concentrated by evaporation to dryness. The residue was triturated with hexane (500 ml) and filtered. The resulting residue was washed with hexane (2×200 ml) and then dried at 35~40° C. to a constant weight to obtain compound 7 (90 g, 95% yield). $^1$H-NMR (CDCl$_3$, 500 MHz): δ 7.81 (d, 1H, J=8.5 Hz), 6.48 (dd, 1H, J=2 & 8.5 Hz), 6.41 (d, 1H, J=2.0 Hz), 4.66-4.59 (m, 2H), 2.59 (s, 3H), 1.42 (d, 6H, J=6.5 Hz), 1.36 (d, 6H, J=6.5 Hz).

Example 10

Synthesis of (E)-1-(2,4-diisopropoxyphenyl)-3-(2,4-dimethoxy-3-methylphenyl)prop-2-en-1-one

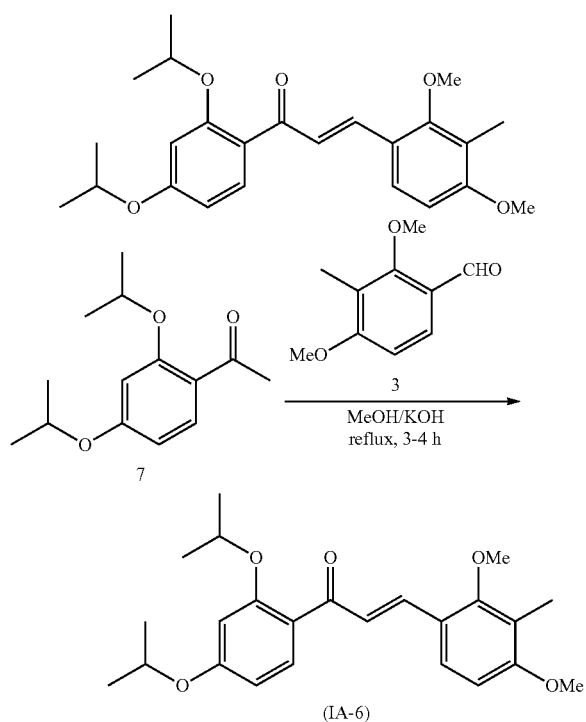

A solution of 2,4-diisopropoxyacetophenone 7 (47.2 g, 0.2 mol) in methanol (200 ml) was cooled to 10~15° C. and treated with potassium hydroxide (56 g, 1 mol) in MeOH (200 ml) over a period of 1.5 h. 2,4-dimethoxy-3-methylbenzaldehyde (43.2 g, 0.24 mol) in MeOH (200 ml) was then added to the reaction mixture over 1.5 h at 10~15° C. After the addition was complete, cooling was removed. The reaction mixture was then heated to 60~65° C. with stirring for approximately 20 h and held at this temperature until determined to be complete by TLC. After completion, the reaction mixture was cooled to 10~15° C. and quenched with 2 N aqueous HCl (150 ml) to pH 2. The solid formed at this stage was filtered, washed with water and dissolved in MeOH (500 ml). This methanol solution was then cooled to 22~25° C. and stirred for 20 min by which time a yellow crystalline solid had formed. The solid was collected by filtration, washed with water and dried under vacuum to a constant weight at 30° C. to obtain (IA-6) (70 g, 88%). $^1$H-NMR (CDCl$_3$, 500 MHz): δ 7.92 (d, 1H, J=16 Hz), 7.75 (d, 1H, J=9 Hz), 7.58 (d, 1H, J=16 Hz), 7.52 (d, 1H, J=9 Hz), 7.69 (d, 1H, J=9 Hz), 6.54 (dd, 1H, J=2 & 9 Hz), 6.46 (d, 1H, J=2 Hz), 4.64-4.59 (m, 2H), 3.87 (s, 3H), 3.66 (s, 3H), 2.17 (s, 3H) 1.38 (d, 16H, J=6 Hz).

Example 11

Synthesis of 1-(3-(2,4-diisopropoxyphenyl)propyl)-2,4-dimethoxy-3-methylbenzene

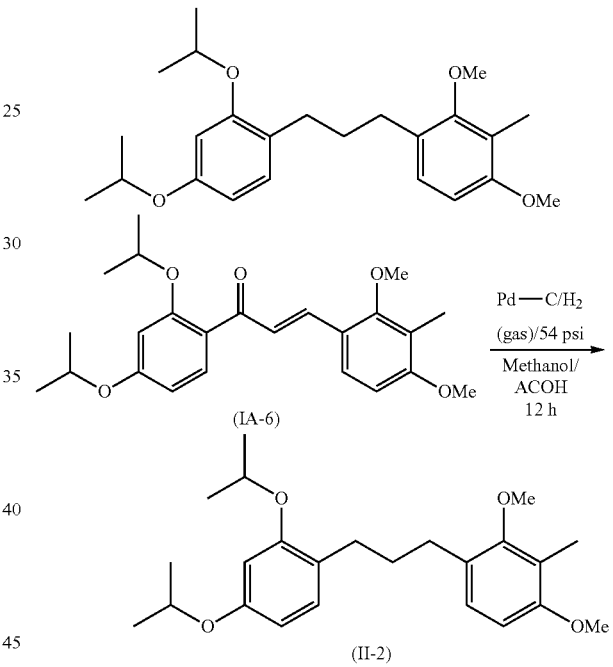

A solution of (IA-6) (60 g, 0.15 mol) in methanol (600 ml) was treated with 10% Pd—C (10% by weight) and acetic acid (60 ml) and hydrogenated under a hydrogen atmosphere at 23~25° C. and 54 psi for 10 h. When the reaction was determined complete by TLC, the reaction mixture was filtered through celite, and the celite bed was washed with ethyl acetate (250 ml). The combined filtrate was then concentrated under vacuum at 35~40° C. to dryness. The residue was dissolved in ethyl acetate (750 ml) and washed sequentially with saturated sodium bicarbonate solution (250 ml) to pH 7~7.5, water (250 ml) and brine. The ethyl acetate layer was dried over sodium sulfate, filtered and then concentrated under vacuum at 35~45° C. to constant weight to yield (II-2) (52 g, 90% yield). $^1$H-NMR (CDCl$_3$, 500 MHz): 7.03 (d, 1H, J=8.5 Hz), 7.00 (d, 1H, J=8.5 Hz), 6.60 (d, 1H, J=8.5 Hz), 6.43 (d, 1H, J=2 Hz), 6.40 (dd, 1H, J=2 & 8.5 Hz), 4.52-4-48 (m, 2H), 3.82 (s, 3H), 3.72 (s, 3H), 2.64-2.59 (m, 4H), 2.17 (s, 3H), 1.33 (d, 6H, J=6 Hz), 1.32 (d, 6H, J=6 Hz); $^{13}$C-NMR (CDCl$_3$, 125 MHz): δ 157.304 (C), 156.996 (C), 156.830 (C), 156.582 (C), 130.004 (CH), 127.791 (C), 126.680 (CH), 124.267 (C), 119.466 (C), 106.151 (CH), 106.018 (CH), 102.512 (CH), 69.957 (CH), 69.731 (CH), 60.525 (CH$_3$), 55.631 (CH$_3$), 31.216 (CH$_2$), 29.794 (CH$_2$), 29.271 (CH$_2$), 22.202 (2, CH$_3$), 22.161 (2, CH$_3$), 9.147 (CH$_3$).

Example 12

Synthesis of 4-(3-(2,4-dimethoxy-3-methylphenyl)propyl)benzene-1,3-diol

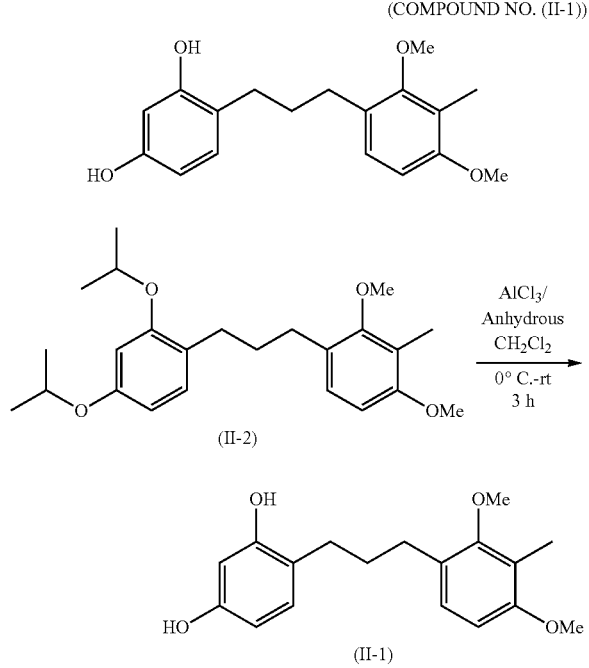

A solution of (II-2) (38.6 g, 0.1 mol) in anhydrous CH$_2$Cl$_2$ (250 ml) was treated with AlCl$_3$ under an argon atmosphere at 0-5° C. The reaction mixture was then stirred for 3 h at room temperature until found complete by TLC. The reaction was then cooled to 0-5° C., quenched with saturated NH$_4$Cl, diluted with water (100 ml) and extracted with ethyl acetate (3×250 ml). The combined ethyl acetate extract was washed with aqueous sodium bicarbonate followed by brine (250 L). The ethyl acetate layer was then dried over dry sodium sulfate and concentrated under vacuum at 40–45° C. The crude product thus obtained was dissolved in MeOH (500 ml) and refluxed for 20 minutes in charcoal (400 g). This suspension was filtered through celite and washed with ethyl acetate (25 L). The filtered solution was concentrated and crystallized in MeOH. The solid thus obtained was dried under vacuum for 8 h at 55-60° C. to produce (II-1) (24.2 g, 60% yield). MP: 108.0° C.; $^1$H-NMR (CDCl$_3$, 500 MHz): δ 6.96 (d, 1H, J=8.3 Hz), 6.85 (d, 1H, J=8.3 Hz), 6.62 (d, 1H, J=8.3 Hz), 6.27 (d, 1H, J=2.2 Hz), 6.21 (dd, 1H, J=2.2 Hz), 3.77 (s, 3H), 3.63 (s, 3H), 2.52-2.58 (m, 4H), 2.10 (s, 3H), 1.78-1.82 (m, 2H); $^{13}$C-NMR (CDCl$_3$, 125 MHz): δ 158.55 (C), 158.43 (C), 157.38 (C), 157.15 (C), 131.53 (CH), 128.95 (C), 128.28 (CH), 121.45 (C), 120.30 (C), 107.40 (CH), 103.60 (CH), 61.44 (CH$_3$), 56.19 (CH$_3$), 32.90 (CH$_2$), 30.77 (CH$_2$), 30.51 (CH$_2$), 9.195 (CH$_3$).

Example 13

Synthesis of 2,4-diisopropoxybenzaldehyde

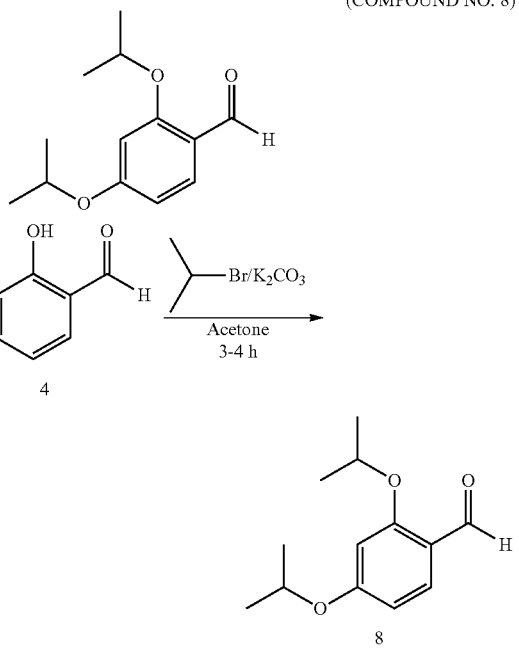

Compound 8 is prepared in a manner analogous to that described in Example 9. Protecting groups are employed as needed.

Example 14

Synthesis of (E)-3-(2,4-diisopropoxyphenyl)-1-(2,4-dimethoxy-3-methylphenyl)prop-2-en-1-one

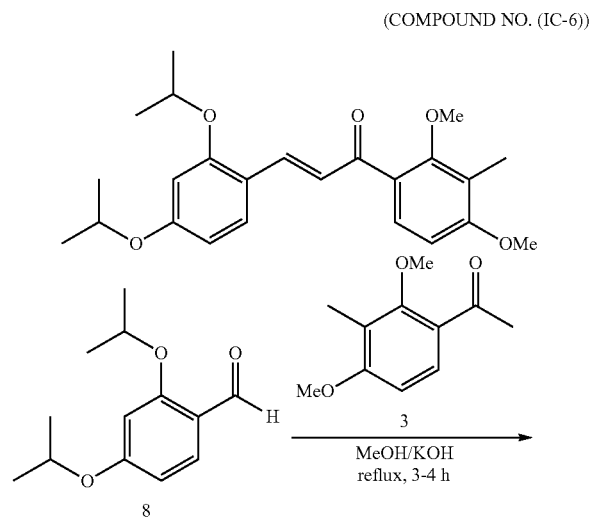

-continued

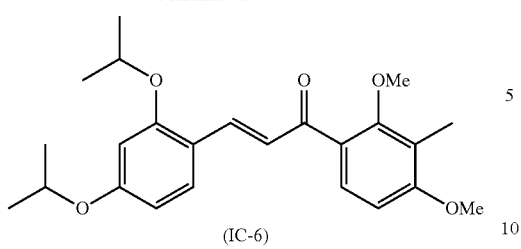

(IC-6)

Compound (IC-6) is prepared by aldol condensation of 8 and 3 in a manner analogous to that described in Example 10.

Example 15

Synthesis of 1-(3-(2,4-diisopropoxyphenyl)propyl)-2,4-dimethoxy-3-methylbenzene (COMPOUND NO. (II-2))

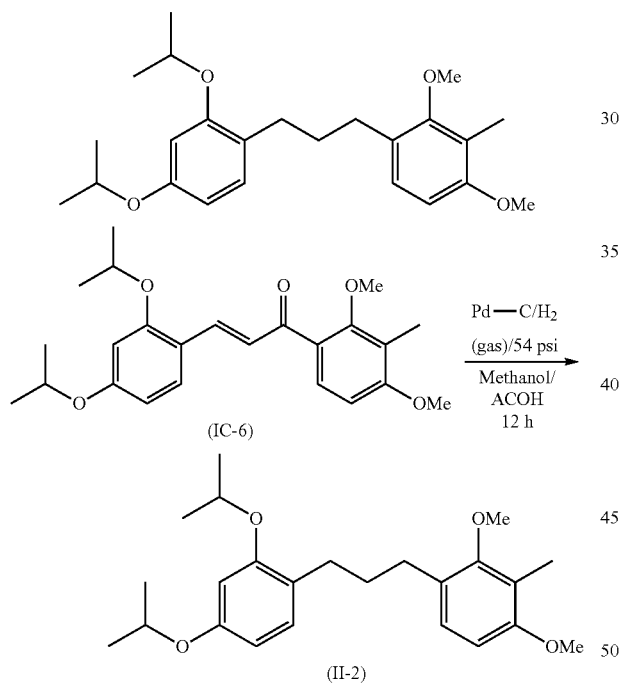

(II-2)

Compound (II-2) is prepared from (IC-6) in a manner analogous to that described in Example 11.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A compound having the following structure (I):

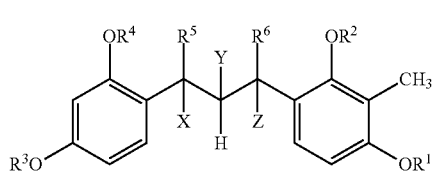

or a stereoisomer, tautomer or salt thereof, wherein:
$R^1$, $R^2$, $R^3$ and $R^4$ are each independently hydrogen, alkyl, aryl or aralkyl;
one of $R^5$ or $R^6$ is oxo, and the other of $R^5$ or $R^6$ is hydrogen; and
X, Y and Z are each independently absent or hydrogen, or X and Y or Z and Y may join to form a bond, wherein X, Y and Z are each chosen such that all valences are satisfied.

2. The compound of claim 1, wherein $R^5$ is oxo, $R^6$ is hydrogen and the compound has one of the following structures (IA) or (IB):

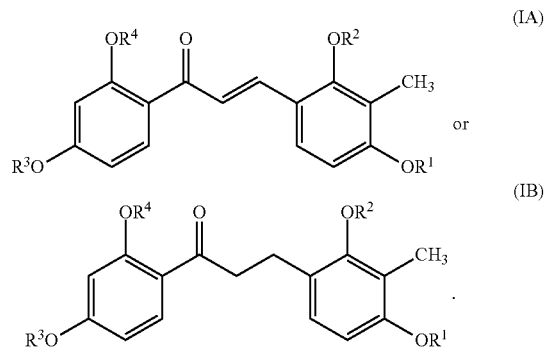

3. The compound of claim 2, wherein each of $R^1$ and $R^2$ are alkyl.

4. The compound of claim 3, wherein each of $R^1$ and $R^2$ are methyl and the compound has one of the following structures (IA-1) or (IB-1):

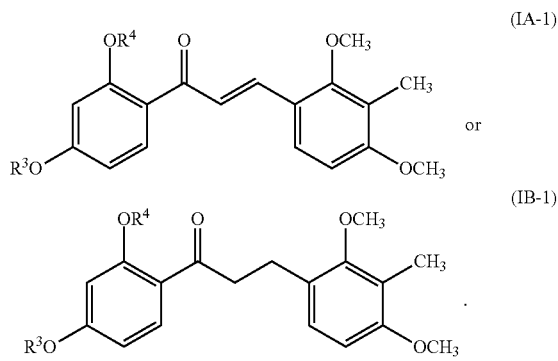

5. The compound of claim 2, wherein each of $R^3$ and $R^4$ are aralkyl.

6. The compound of claim 5, wherein each of $R^3$ and $R^4$ are benzyl and the compound has one of the following structures (IA-2) or (IB-2):

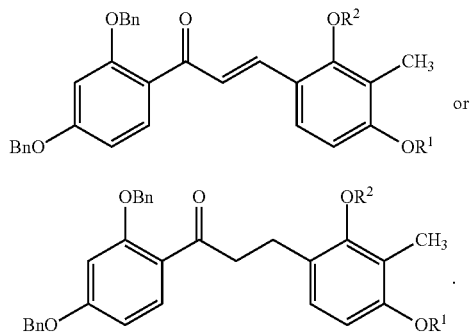

(IA-2)

(IB-2)

7. The compound of claim 2, wherein each of $R^3$ and $R^4$ are alkyl.

8. The compound of claim 7, wherein each of $R^3$ and $R^4$ are isopropyl and the compound has one of the following structures (IA-3) or (IB-3):

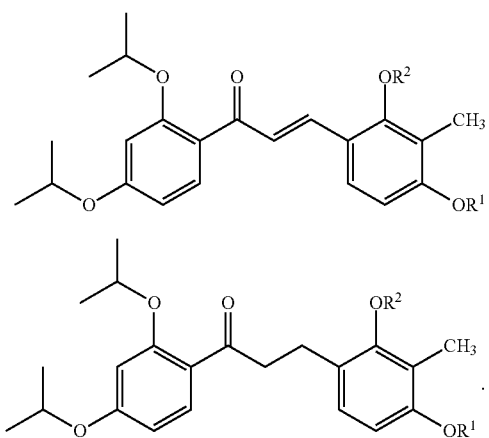

(IA-3)

(IB-3)

9. The compound of claim 2, wherein each of $R^3$ and $R^4$ are hydrogen and the compound has one of the following structures (IA-4) or (IB-4):

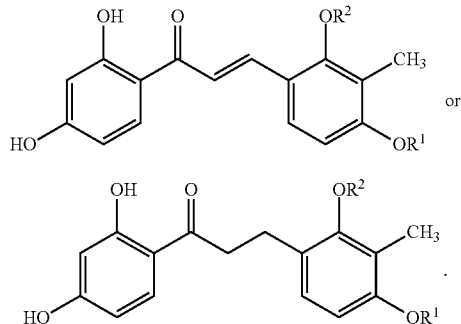

(IA-4)

(IB-4)

10. The compound of claim 1, wherein $R^6$ is oxo, $R^5$ is hydrogen and the compound has one of the following structures (IC) or (ID):

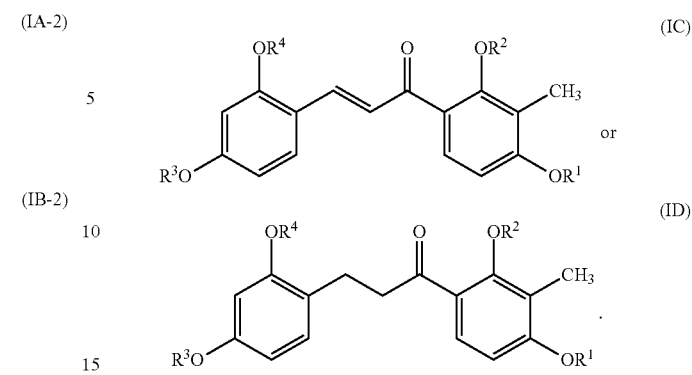

(IC)

(ID)

11. The compound of claim 10, wherein each of $R^1$ and $R^2$ are alkyl.

12. The compound of claim 11, wherein each of $R^1$ and $R^2$ are methyl and the compound has one of the following structures (IC-1) or (ID-1):

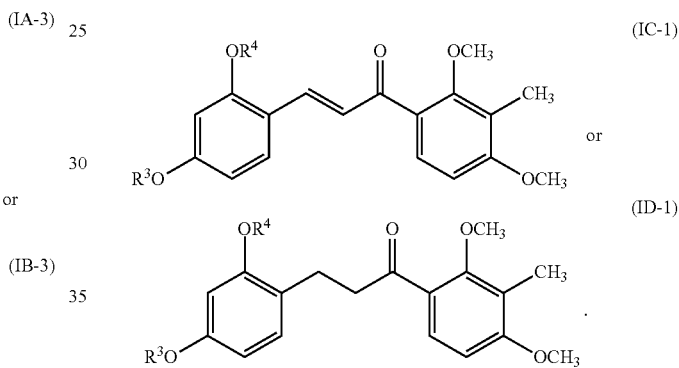

(IC-1)

(ID-1)

13. The compound of claim 10, wherein each of $R^3$ and $R^4$ are aralkyl.

14. The compound of claim 13, wherein each of $R^3$ and $R^4$ are benzyl and the compound has one of the following structures (IC-2) or (ID-2):

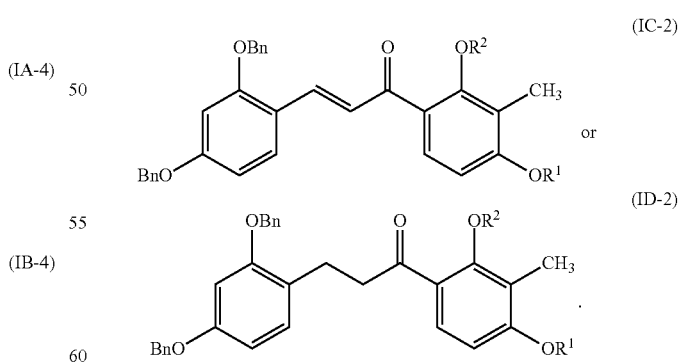

(IC-2)

(ID-2)

15. The compound of claim 10, wherein each of $R^3$ and $R^4$ are alkyl.

16. The compound of claim 15, wherein each of $R^3$ and $R^4$ are isopropyl and the compound has one of the following structures (IC-3) or (ID-3):

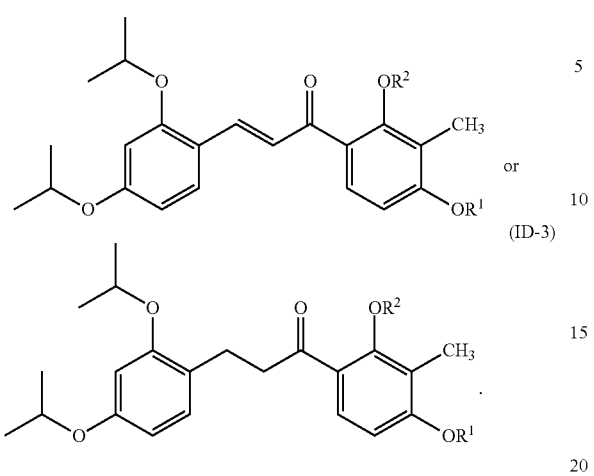

17. The compound of claim 10, wherein each of $R^3$ and $R^4$ are hydrogen and the compound has one of the following structures (IC-4) or (ID-4):

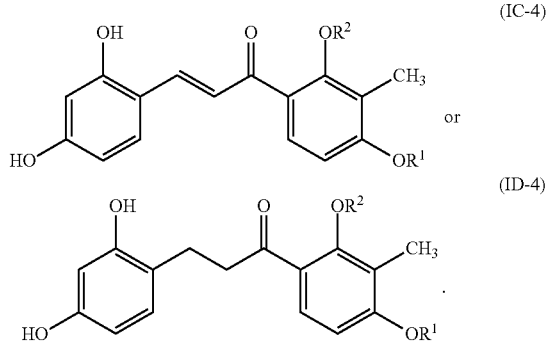

18. The compound of claim 1, wherein at least one of $R^3$ or $R^4$ is allyl.

19. The compound of claim 18, wherein each of $R^3$ and $R^4$ are allyl.

20. The compound of claim 18, wherein at least one of $R^1$ or $R^2$ is methyl.

21. The compound of claim 20, wherein each of $R^1$ and $R^2$ is methyl.

22. The compound of claim 1, wherein at least one of $R^3$ or $R^4$ is aralkyl.

23. The compound of claim 1, wherein at least one of $R^3$ or $R^4$ is alkyl.

24. The compound of claim 1, wherein the compound has one of the following structures (IA-5), (IA-6), (IA-7) or (IA-8):

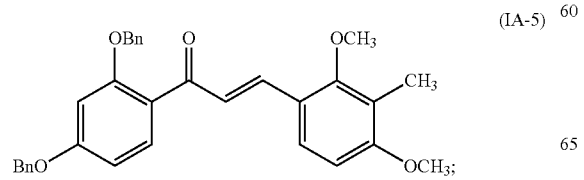

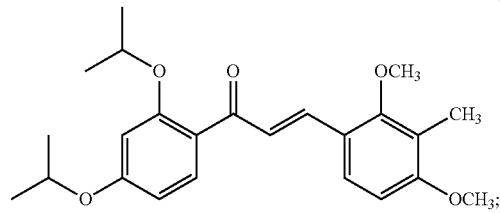

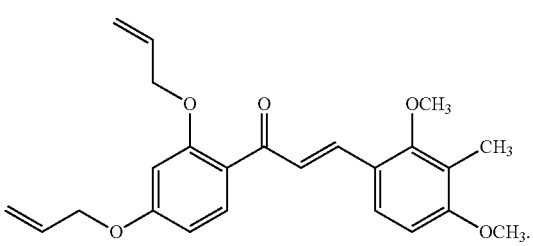

25. The compound of claim 1, wherein the compound has one of the following structures (IB-5), (IB-6), (IB-7) or (IB-8):

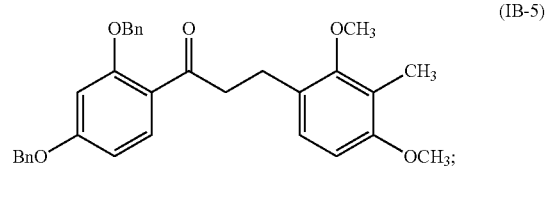

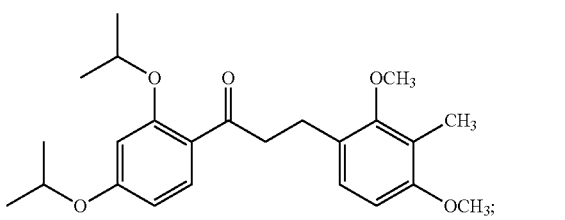

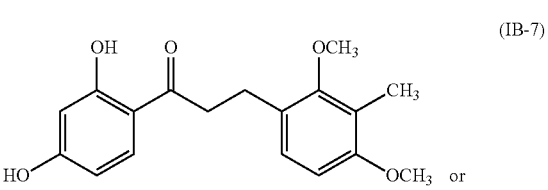

(IB-8)

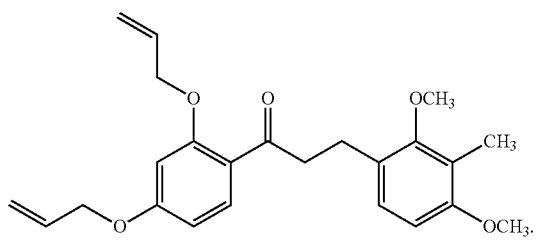

26. The compound of claim 1, wherein the compound has one of the following structures (IC-5), (IC-6), (IC-7) or (IC-8):

(IC-5)

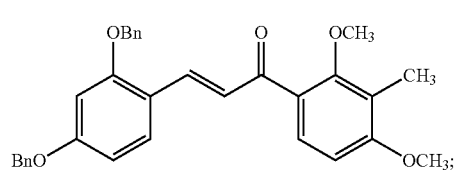

(IC-6)

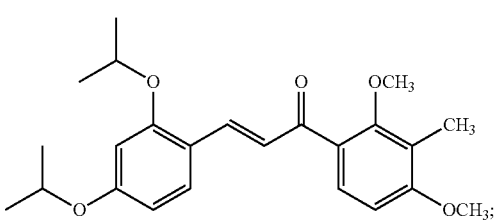

(IC-7)

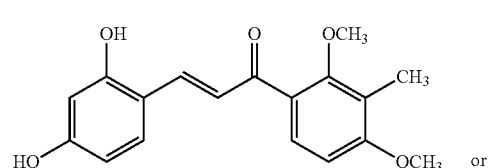

or (IC-8)

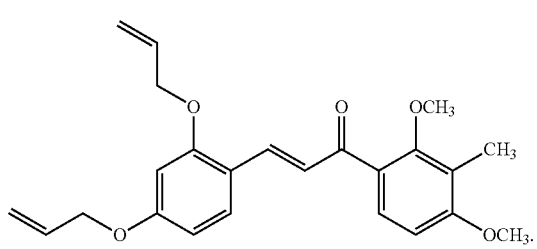

27. The compound of claim 1, wherein the compound has one of the following structures (ID-5), (ID-6), (ID-7) or (ID-8):

(ID-5)

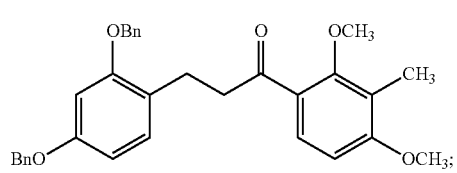

(ID-6)

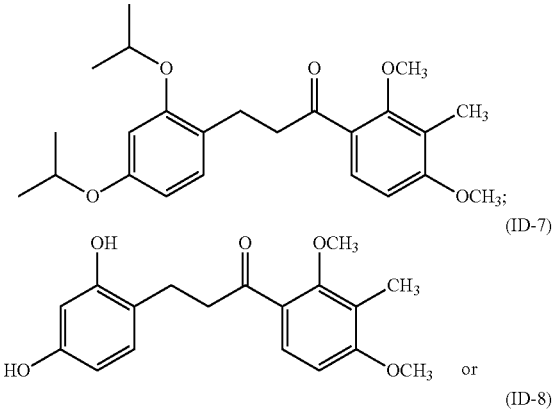

(ID-7)

or (ID-8)

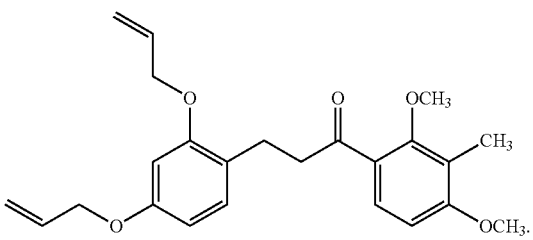

28. A method for preparing a compound of structure (II):

(II)

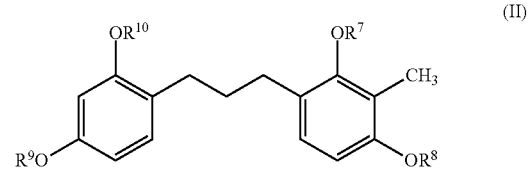

or a stereoisomer, tautomer or salt thereof, wherein:
$R^7$, $R^8$, $R^9$ and $R^{10}$ are each independently hydrogen, alkyl, aryl or aralkyl, the method comprising reducing a compound of structure (I):

(I)

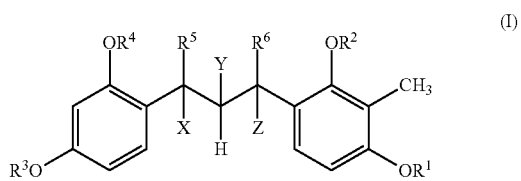

or a stereoisomer, tautomer or salt thereof, wherein:
$R^1$, $R^2$, $R^3$ and $R^4$ are each independently hydrogen, alkyl, aryl or aralkyl;
one of $R^5$ or $R^6$ is oxo, and the other of $R^5$ or $R^6$ is hydrogen; and
X, Y and Z are each independently absent or hydrogen, or X and Y or Z and Y may join to form a bond, wherein X, Y and Z are each chosen such that all valences are satisfied.

29. The method of claim 28, wherein the compound of structure (I) has one of the following structures (IB) or (ID):

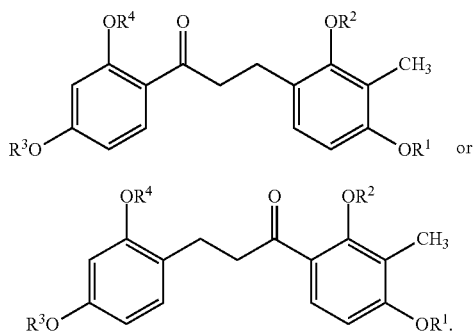
(IB)

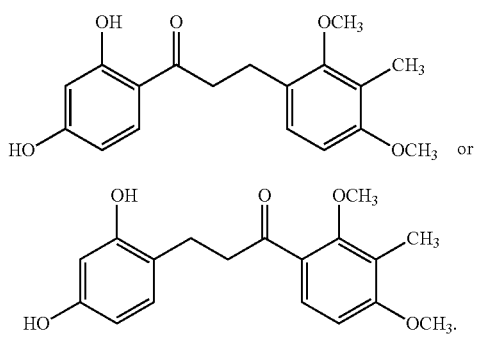
(ID)

30. The method of claim 29, wherein each of $R^1$ and $R^2$ are methyl.

31. The method of claim 29, wherein each of $R^3$ and $R^4$ are hydrogen.

32. The method of claim 29, wherein each of $R^1$ and $R^2$ are methyl, each of $R^3$ and $R^4$ are hydrogen and the compound of structure (I) has one of the following structures (IB-7) or (ID-7):

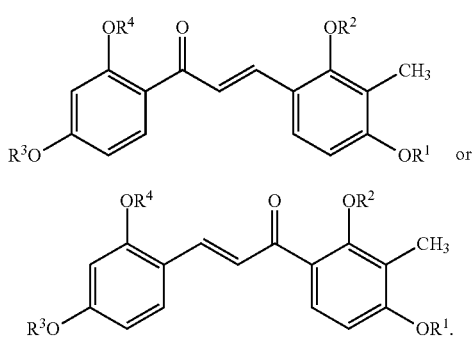
(IB-7)
(ID-7)

33. The method of claim 29, wherein reducing comprises treating a compound of structure (IB) or (ID) with sodium bis(2-methoxyethoxy)aluminum hydride, Raney nickel and hydrogen gas or zinc/HCl.

34. The method of claim 29, wherein the compound of structure (IB) or (ID) has been prepared by reducing a compound of structure (IA) or (IC), respectively:

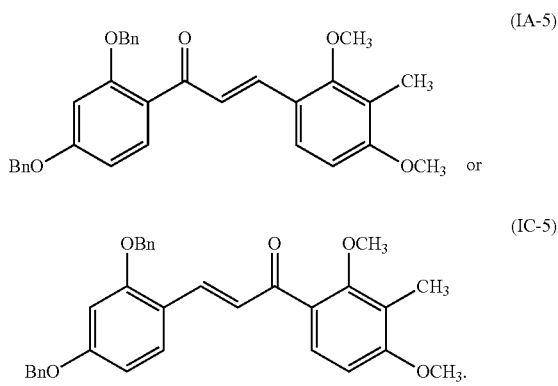
(IA)
(IC)

35. The method of claim 34, wherein each of $R^1$ and $R^2$ are methyl.

36. The method of claim 34, wherein each of $R^3$ and $R^4$ are benzyl.

37. The method of claim 34, wherein each of $R^3$ and $R^4$ are isopropyl.

38. The method of claim 34, wherein each of $R^1$ and $R^2$ are methyl, each of $R^3$ and $R^4$ are benzyl and the compound of structure (I) has one of the following structures (IA-5) or (IC-5):

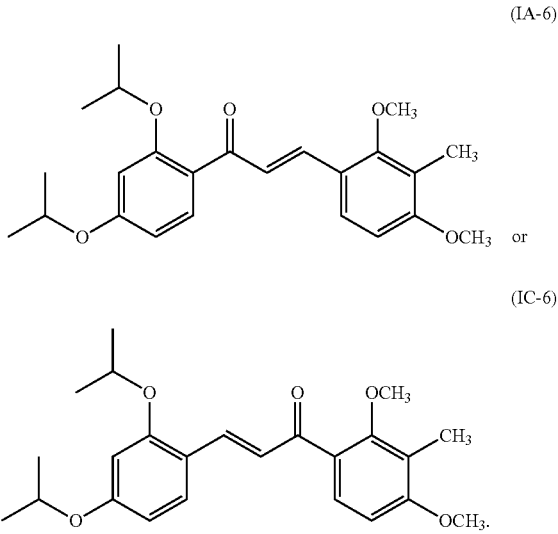
(IA-5)
(IC-5)

39. The method of claim 34, wherein each of $R^1$ and $R^2$ are methyl, each of $R^3$ and $R^4$ are isopropyl and the compound of structure (I) has one of the following structures (IA-6) or (IC-6):

(IA-6)

(IC-6)

40. The method of claim 34, wherein reducing comprises treating a compound of structure (IA) or (IC) with palladium on carbon and formic acid/$H_2$ (gas) or palladium on carbon and ammonium formate.

41. The method of claim 28, wherein the compound of structure (I) has been prepared by reaction of a compound of structure (III) and a compound of structure (IV):

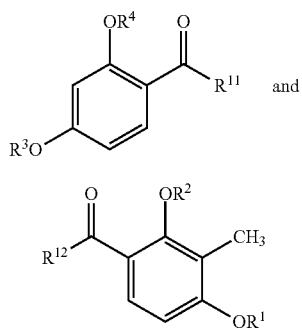

(III)

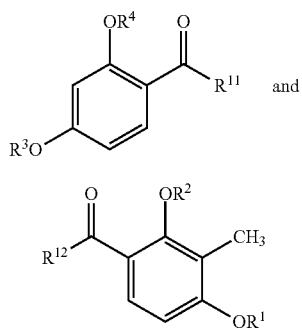

(IV)

or a stereoisomer, tautomer or salt thereof, wherein one of $R^{11}$ or $R^{12}$ is hydrogen and the other of $R^{11}$ or $R^{12}$ is methyl.

42. The method of claim 41, wherein $R^{11}$ is hydrogen and $R^{12}$ is methyl.

43. The method of claim 41, wherein $R^{11}$ is methyl and $R^{12}$ is hydrogen.

44. The method of claim 41, wherein each of $R^1$ and $R^2$ are methyl.

45. The method of claim 41, wherein each of $R^3$ and $R^4$ are benzyl.

46. The method of claim 41, wherein each of $R^3$ and $R^4$ are isopropyl.

47. The method of claim 28, wherein the compound of structure (I) has one of the following structures (IB) or (ID):

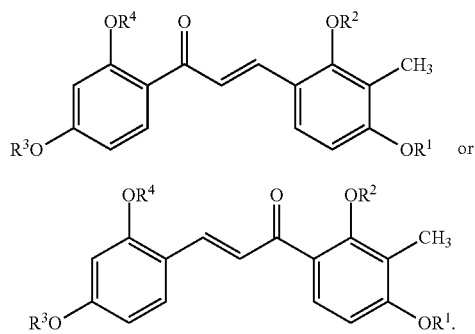

(IA)

(IC)

48. The method of claim 47, wherein each of $R^1$ and $R^2$ are methyl.

49. The method of claim 47, wherein each of $R^3$ and $R^4$ are benzyl.

50. The method of claim 47, wherein each of $R^3$ and $R^4$ are isopropyl.

51. The method of claim 47, wherein each of $R^1$ and $R^2$ are methyl, each of $R^3$ and $R^4$ are benzyl and the compound of structure (I) has one of the following structures (IA-5) or (IC-5):

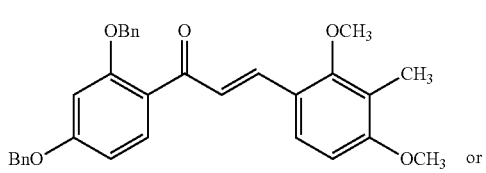

(IA-5)

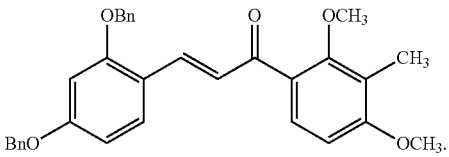

(IC-5)

52. The method of claim 51, wherein reducing comprises the steps of:

(a) treatment with palladium on carbon and formic acid/$H_2$ (gas) or palladium on carbon and ammonium formate; and (b) treatment with sodium bis(2-methoxyethoxy)aluminum hydride, Raney nickel and hydrogen gas or zinc/HCl.

53. The method of claim 47, wherein each of $R^1$ and $R^2$ are methyl, each of $R^3$ and $R^4$ are isopropyl and the compound of structure (I) has one of the following structures (IA-6) or (IC-6):

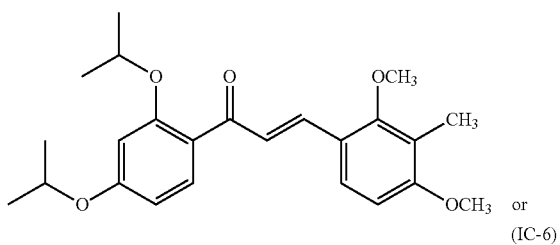

(IA-6)

(IC-6)

54. The method of claim 53, wherein reducing comprises treating a compound of structure (IA-6) or (IC-6) with palladium on carbon, hydrogen gas and acetic acid.

55. The method of claim 28, wherein the compound of structure (II) has the following structure (II-2):

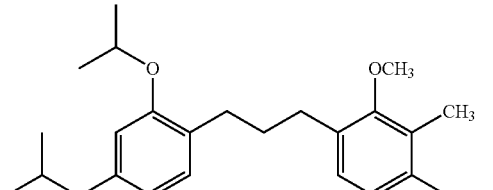

(II-2)

56. The method of claim 28, wherein the compound of structure (II) has the following structure (II-1):

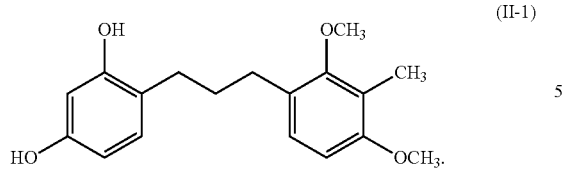
(II-1)
57. The method of claim 28, wherein at least one of $R^3$ or $R^4$ is allyl.
58. The method of claim 57, wherein each of $R^3$ and $R^4$ are allyl.
59. The method of claim 28, wherein at least one of $R^3$ or $R^4$ is benzyl.
* * * * *